(12) United States Patent
Hulliger

(10) Patent No.: US 10,052,143 B2
(45) Date of Patent: Aug. 21, 2018

(54) TENSIONING INSTRUMENT AND RELATED BONE FIXATION SYSTEMS AND METHODS

(71) Applicant: DePuy Synthes Products, Inc., Raynham, MA (US)

(72) Inventor: Urs Hulliger, Deitingen (CH)

(73) Assignee: Depuy Synthes Products, Inc., Raynham, MA (US)

(*) Notice: Subject to any disclaimer, the term of this patent is extended or adjusted under 35 U.S.C. 154(b) by 518 days.

(21) Appl. No.: 14/694,260

(22) Filed: Apr. 23, 2015

(65) Prior Publication Data

US 2015/0313656 A1 Nov. 5, 2015

Related U.S. Application Data

(60) Provisional application No. 61/986,434, filed on Apr. 30, 2014.

(51) Int. Cl.
*A61B 17/82* (2006.01)
*A61B 17/84* (2006.01)
(Continued)

(52) U.S. Cl.
CPC ............ *A61B 17/82* (2013.01); *A61B 17/823* (2013.01); *A61B 17/842* (2013.01);
(Continued)

(58) Field of Classification Search
CPC ... A61B 17/82; A61B 17/823; A61B 17/8861; A61B 17/8863; A61B 17/8869; A61B 17/8872
(Continued)

(56) References Cited

U.S. PATENT DOCUMENTS 257,389 A 5/1882 Sager
276,135 A 4/1883 Cooley
(Continued)

FOREIGN PATENT DOCUMENTS

DE 744614 1/1944
DE 1089116 9/1960
(Continued)

OTHER PUBLICATIONS

Chevalier, "Guide De Dessinateur Industeriel", Edition 1984-1985, 7 pages.
(Continued)

*Primary Examiner* — Eric S Gibson
(74) *Attorney, Agent, or Firm* — Baker & Hostetler LLP

(57) ABSTRACT

An instrument includes a bearing member, and an actuator spaced from the bearing member in a proximal direction. The instrument includes, or can be attached to, an elongate member that extends from a location of the actuator toward the bearing member. The elongate member can attach to or extend from a portion of an implant, wherein the location is spaced from the bearing member a distance in the proximal direction. The actuator includes a flexible portion that is spaced from the elongate member in a direction perpendicular to the proximal direction, such that, when a force is applied to the flexible portion of the actuator, the flexible portion of the actuator deforms so as to increase the distance between the location and the bearing member.

20 Claims, 27 Drawing Sheets

(51) Int. Cl.
*A61B 17/88* (2006.01)
*A61B 17/68* (2006.01)
(52) U.S. Cl.
CPC ...... *A61B 17/8861* (2013.01); *A61B 17/8863* (2013.01); *A61B 17/8869* (2013.01); *A61B 17/8872* (2013.01); *A61B 2017/681* (2013.01)
(58) Field of Classification Search
USPC .................................................. 606/74, 103
See application file for complete search history.

(56) References Cited

U.S. PATENT DOCUMENTS

| | | | |
|---|---|---|---|
| 460,222 A | 9/1891 | Silsby | |
| 601,399 A | 3/1898 | Manix | |
| 741,747 A | 10/1903 | Walz | |
| 891,509 A | 6/1908 | Tanner | |
| 1,304,620 A | 5/1919 | Steinkoenig et al. | |
| 1,429,580 A | 9/1922 | Geiger | |
| 1,510,416 A | 9/1924 | Pietz et al. | |
| 1,561,119 A | 11/1925 | Smith | |
| 1,641,077 A | 8/1927 | Fouguet | |
| 1,918,700 A | 7/1933 | Harris | |
| 2,049,936 A | 8/1936 | Zimmer | |
| 2,118,561 A | 5/1938 | Kleeberg | |
| 2,217,077 A | 10/1940 | Phillips | |
| 2,275,058 A | 3/1942 | Draving | |
| 2,279,068 A * | 4/1942 | Siebrandt | A61B 17/8861 |
| | | | 140/121 |
| 2,291,413 A | 7/1942 | Siebrandt | |
| 2,315,326 A | 3/1943 | Gmeiner | |
| 2,316,297 A | 4/1943 | Southerland et al. | |
| 2,340,995 A | 2/1944 | Smith | |
| 2,343,079 A | 2/1944 | Pickwell | |
| 2,447,319 A | 7/1948 | De Fourchambault | |
| 2,480,783 A | 8/1949 | Sloan | |
| 2,485,531 A | 10/1949 | Dzus et al. | |
| 2,576,649 A | 11/1951 | Slind et al. | |
| 2,875,779 A | 3/1959 | Campbell | |
| 3,021,129 A | 2/1962 | Maker | |
| 3,038,626 A | 6/1962 | Simmons | |
| 3,047,945 A * | 8/1962 | Logan | B65B 13/027 |
| | | | 140/123.6 |
| 3,068,666 A | 12/1962 | Sabadash | |
| 3,168,119 A * | 2/1965 | Schwester | B65B 13/027 |
| | | | 140/123.6 |
| 3,169,560 A * | 2/1965 | Caveney | B65B 13/027 |
| | | | 140/123.6 |
| 3,175,556 A | 3/1965 | Wood et al. | |
| 3,259,383 A | 7/1966 | Johnson | |
| 3,370,621 A * | 2/1968 | Brohawn | B65B 13/025 |
| | | | 140/123.6 |
| 3,376,727 A | 4/1968 | Hinden | |
| 3,390,546 A | 7/1968 | Jewell | |
| 3,507,284 A | 4/1970 | Simmons et al. | |
| 3,537,275 A | 11/1970 | Smith | |
| 3,540,106 A | 11/1970 | Goldman | |
| 3,588,291 A | 6/1971 | Curwen et al. | |
| 3,645,302 A * | 2/1972 | Caveney | B65B 13/027 |
| | | | 140/123.6 |
| 3,763,560 A | 10/1973 | Makkay et al. | |
| 3,810,499 A | 5/1974 | Benfer | |
| 3,830,263 A * | 8/1974 | Benfer | B21F 9/02 |
| | | | 140/93.2 |
| 3,906,774 A | 9/1975 | LaPointe | |
| 3,908,268 A | 9/1975 | Brown | |
| 3,959,960 A * | 6/1976 | Santos | A61B 17/04 |
| | | | 57/22 |
| 3,971,384 A | 7/1976 | Hasson | |
| 4,050,464 A * | 9/1977 | Hall | A61B 17/025 |
| | | | 29/268 |
| 4,088,134 A | 5/1978 | Mazzariello | |
| 4,093,005 A * | 6/1978 | Eberhardt | B65B 13/027 |
| | | | 140/123.6 |
| 4,202,384 A * | 5/1980 | Aubert | B65B 13/027 |
| | | | 140/123.6 |
| 4,203,305 A | 5/1980 | Williams | |
| 4,246,698 A | 1/1981 | Lasner et al. | |
| 4,321,952 A | 3/1982 | Natkins | |
| 4,367,746 A | 1/1983 | Derechinsky | |
| 4,395,824 A | 8/1983 | Puro | |
| 4,404,746 A | 9/1983 | Jansson et al. | |
| 4,449,429 A | 5/1984 | Sauer et al. | |
| 4,452,246 A | 6/1984 | Bader et al. | |
| 4,587,963 A | 5/1986 | Leibinger et al. | |
| 4,627,164 A | 12/1986 | Mikic et al. | |
| 4,644,953 A | 2/1987 | Lahodny et al. | |
| 4,669,473 A | 6/1987 | Richards et al. | |
| 4,733,701 A | 3/1988 | Loisel et al. | |
| 4,763,669 A | 8/1988 | Jaeger | |
| 4,889,110 A | 12/1989 | Galline et al. | |
| 4,924,709 A | 5/1990 | Plyter | |
| 4,928,738 A | 5/1990 | Hinnen et al. | |
| 4,932,638 A | 6/1990 | Chen | |
| 4,950,284 A | 8/1990 | Green et al. | |
| 4,966,600 A | 10/1990 | Songer et al. | |
| 5,000,232 A | 3/1991 | Wolcott | |
| 5,027,867 A | 7/1991 | O'Connor | |
| 5,030,050 A | 7/1991 | Auriol et al. | |
| 5,048,575 A | 9/1991 | Smith | |
| 5,057,113 A * | 10/1991 | Mingozzi | A61B 17/8869 |
| | | | 606/103 |
| 5,059,193 A | 10/1991 | Kuslich | |
| 5,083,350 A | 1/1992 | Sandreid | |
| 5,098,433 A | 3/1992 | Freedland | |
| 5,111,853 A | 5/1992 | Scruggs | |
| 5,116,340 A * | 5/1992 | Songer | A61B 17/8861 |
| | | | 29/282 |
| 5,167,582 A | 12/1992 | Hunt | |
| 5,250,049 A | 10/1993 | Michael | |
| 5,258,015 A | 11/1993 | Li et al. | |
| 5,268,001 A | 12/1993 | Nicholson et al. | |
| 5,282,807 A | 2/1994 | Knoepfler | |
| 5,312,410 A * | 5/1994 | Miller | A61B 17/8861 |
| | | | 606/103 |
| 5,323,521 A * | 6/1994 | Freund | B21J 15/043 |
| | | | 29/243.527 |
| 5,339,870 A | 8/1994 | Green et al. | |
| 5,342,393 A | 8/1994 | Stack | |
| 5,345,663 A | 9/1994 | Scruggs | |
| 5,350,399 A | 9/1994 | Eriebacher et al. | |
| 5,361,475 A | 11/1994 | Scruggs | |
| 5,370,646 A | 12/1994 | Reese et al. | |
| 5,372,166 A | 12/1994 | Lai | |
| 5,386,856 A * | 2/1995 | Moody | B65B 13/027 |
| | | | 140/123.5 |
| 5,388,619 A * | 2/1995 | Ghawi | A61B 17/42 |
| | | | 140/123.6 |
| 5,392,822 A | 2/1995 | Kraus | |
| 5,417,698 A * | 5/1995 | Green | A61B 17/8861 |
| | | | 140/123.5 |
| 5,423,817 A | 6/1995 | Lin | |
| 5,431,659 A * | 7/1995 | Ross, Jr. | A61B 17/8869 |
| | | | 140/123.5 |
| 5,449,361 A | 9/1995 | Preissman | |
| 5,468,242 A | 11/1995 | Reisberg | |
| 5,476,465 A | 12/1995 | Preissman | |
| 5,511,589 A | 4/1996 | Scruggs | |
| 5,531,297 A | 7/1996 | Pipan | |
| 5,531,750 A | 7/1996 | Even-Esh | |
| 5,536,270 A * | 7/1996 | Songer | A61B 17/823 |
| | | | 606/103 |
| 5,538,427 A | 7/1996 | Hoffman et al. | |
| 5,540,697 A | 7/1996 | Rehmann et al. | |
| 5,540,698 A * | 7/1996 | Preissman | A61B 17/82 |
| | | | 606/103 |
| 5,545,168 A | 8/1996 | Burke | |
| 5,569,253 A | 10/1996 | Farris et al. | |
| 5,600,878 A | 2/1997 | Byrne et al. | |
| 5,632,312 A | 5/1997 | Hoffman | |
| 5,666,710 A | 9/1997 | Weber | |
| 5,720,747 A | 2/1998 | Burke | |

(56) References Cited

U.S. PATENT DOCUMENTS

| | | | |
|---|---|---|---|
| 5,743,310 A | 4/1998 | Moran | |
| 5,749,899 A | 5/1998 | Bardin | |
| 5,752,959 A * | 5/1998 | Korhonen | A61B 17/8861 606/103 |
| 5,800,436 A | 9/1998 | Lerch | |
| 5,814,048 A | 9/1998 | Morgan | |
| 5,832,964 A | 11/1998 | Joshi | |
| 5,868,748 A | 2/1999 | Burke | |
| 5,893,850 A | 4/1999 | Cachia | |
| 5,902,305 A | 5/1999 | Beger et al. | |
| 5,925,050 A | 7/1999 | Howard, III | |
| 5,928,244 A | 7/1999 | Tovey et al. | |
| 5,935,130 A | 8/1999 | Kilpela et al. | |
| 5,935,133 A | 8/1999 | Wagner et al. | |
| 5,944,302 A | 8/1999 | Loc et al. | |
| 5,961,519 A | 10/1999 | Bruce et al. | |
| 5,966,815 A | 10/1999 | Sheikh | |
| 6,010,513 A | 1/2000 | Tormala et al. | |
| 6,021,553 A | 2/2000 | Beiber et al. | |
| 6,022,351 A | 2/2000 | Bremer et al. | |
| 6,068,631 A | 5/2000 | Lerch | |
| 6,123,711 A | 9/2000 | Winters | |
| 6,126,663 A | 10/2000 | Hair | |
| 6,168,596 B1 | 1/2001 | Weillisz et al. | |
| 6,203,437 B1 | 3/2001 | Durie et al. | |
| 6,228,087 B1 | 5/2001 | Fenaroli et al. | |
| 6,241,732 B1 | 6/2001 | Overaker et al. | |
| 6,328,743 B2 | 12/2001 | Lerch | |
| 6,361,538 B1 | 3/2002 | Fenaroli et al. | |
| 6,368,326 B1 | 4/2002 | Dakin et al. | |
| 6,371,958 B1 | 4/2002 | Overaker | |
| 6,378,289 B1 | 4/2002 | Trudeau et al. | |
| 6,379,363 B1 * | 4/2002 | Herrington | A61B 17/688 606/104 |
| 6,443,955 B1 * | 9/2002 | Ahrend | A61B 17/8866 606/103 |
| 6,485,493 B1 | 11/2002 | Bremer | |
| 6,526,661 B1 | 3/2003 | Shutts et al. | |
| 6,599,295 B1 | 7/2003 | Tornier et al. | |
| 6,641,588 B2 | 11/2003 | Citron et al. | |
| D488,229 S | 4/2004 | Rinner et al. | |
| 6,751,841 B2 | 6/2004 | Schnabel et al. | |
| 7,017,344 B2 | 3/2006 | Pellizzari et al. | |
| 7,037,311 B2 | 5/2006 | Parkinson et al. | |
| 7,048,737 B2 | 5/2006 | Weillisz et al. | |
| 7,048,738 B1 | 5/2006 | Weillisz et al. | |
| 7,059,362 B2 | 6/2006 | Koons et al. | |
| 7,060,067 B2 | 6/2006 | Needham et al. | |
| 7,063,110 B2 | 6/2006 | Chen | |
| 7,063,704 B2 | 6/2006 | Citron et al. | |
| 7,089,970 B2 | 8/2006 | Bernard | |
| 7,168,457 B2 | 1/2007 | Bernard | |
| 7,299,830 B2 | 11/2007 | Levin et al. | |
| 7,361,178 B2 | 4/2008 | Hearn et al. | |
| 7,387,633 B2 | 6/2008 | Ahmad et al. | |
| 7,422,037 B2 | 9/2008 | Levin et al. | |
| 7,806,895 B2 | 10/2010 | Weier et al. | |
| 7,867,262 B2 | 1/2011 | Morales et al. | |
| 7,993,349 B2 | 8/2011 | Hearn et al. | |
| 8,048,077 B2 | 11/2011 | Morales et al. | |
| 8,096,999 B2 * | 1/2012 | Nesper | A61B 17/8869 606/105 |
| 8,292,893 B2 | 10/2012 | Lutze et al. | |
| 8,316,895 B2 | 11/2012 | Hillegonds et al. | |
| 8,500,739 B2 * | 8/2013 | Schoutens | A61B 17/688 140/123.6 |
| 9,351,765 B2 * | 5/2016 | Schoutens | A61B 17/688 |
| 9,603,646 B2 * | 3/2017 | Voisard | A61B 17/8861 |
| 2001/0049529 A1 | 12/2001 | Cachia et al. | |
| 2002/0004661 A1 | 1/2002 | Sevrain et al. | |
| 2002/0016593 A1 | 2/2002 | Hearn et al. | |
| 2002/0029042 A1 | 3/2002 | Fenaroli et al. | |
| 2002/0032450 A1 * | 3/2002 | Trudeau | A61B 17/8861 606/103 |
| 2002/0040224 A1 | 4/2002 | Lerch | |
| 2002/0062128 A1 | 5/2002 | Amis | |
| 2002/0095156 A1 | 7/2002 | Kuras et al. | |
| 2002/0120274 A1 | 8/2002 | Overaker et al. | |
| 2002/0120281 A1 | 8/2002 | Overaker | |
| 2002/0120282 A1 * | 8/2002 | Kilpela | A61B 17/82 606/157 |
| 2002/0169455 A1 | 11/2002 | Bannerman et al. | |
| 2002/0169463 A1 * | 11/2002 | Citron | A61B 17/688 606/148 |
| 2003/0193046 A1 | 10/2003 | Chen | |
| 2004/0059357 A1 * | 3/2004 | Koseki | A61B 17/823 606/151 |
| 2005/0137608 A1 * | 6/2005 | Hearn | A61B 17/688 606/103 |
| 2005/0177179 A1 * | 8/2005 | Baynham | A61B 17/82 606/151 |
| 2005/0178461 A1 * | 8/2005 | Magno, Jr. | B65B 13/027 140/123.6 |
| 2005/0240189 A1 | 10/2005 | Rousseau et al. | |
| 2005/0240191 A1 | 10/2005 | Albertson et al. | |
| 2005/0268983 A1 | 12/2005 | Levin et al. | |
| 2006/0064110 A1 * | 3/2006 | Nesper | A61B 17/688 606/105 |
| 2007/0260251 A1 | 11/2007 | Weier et al. | |
| 2007/0261754 A1 | 11/2007 | Crittenden | |
| 2008/0249532 A1 * | 10/2008 | Schoutens | A61B 17/688 606/60 |
| 2008/0275511 A1 * | 11/2008 | Weinacker | A61B 17/688 606/324 |
| 2009/0044709 A1 | 2/2009 | Hillegonds et al. | |
| 2010/0042106 A1 * | 2/2010 | Bryant | A61B 17/8869 606/103 |
| 2010/0094294 A1 * | 4/2010 | Gillard | A61B 17/823 606/74 |
| 2010/0094362 A1 | 4/2010 | Lutze et al. | |
| 2012/0067450 A1 | 3/2012 | Shafer et al. | |
| 2012/0101536 A1 * | 4/2012 | Nesper | A61B 17/688 606/86 R |
| 2012/0197256 A1 * | 8/2012 | Knueppel | A61B 17/823 606/74 |
| 2013/0018375 A1 * | 1/2013 | Dell'Oca | A61B 17/82 606/74 |
| 2013/0110181 A1 * | 5/2013 | Piotrowski | A61B 17/688 606/324 |
| 2013/0116736 A1 * | 5/2013 | De Oliveira | A61B 17/0467 606/86 R |
| 2013/0310885 A1 | 11/2013 | Schoutens et al. | |
| 2015/0313656 A1 * | 11/2015 | Hulliger | A61B 17/823 606/74 |
| 2015/0342654 A1 * | 12/2015 | Gephart | A61B 17/8869 606/74 |

FOREIGN PATENT DOCUMENTS

| | | |
|---|---|---|
| DE | 2824071 | 12/1978 |
| DE | 3124648 | 1/1983 |
| DE | 19634697 | 4/1998 |
| DE | 19634699 | 4/1998 |
| DE | 29812989 | 9/1998 |
| DE | 29812988 | 11/1998 |
| DE | 19832798 | 11/1999 |
| DE | 19832799 A1 | 1/2000 |
| DE | 19952359 | 3/2001 |
| DE | 20101793 | 5/2001 |
| DE | 20109893 | 8/2001 |
| DE | 20109894 | 9/2001 |
| EP | 0372306 | 6/1990 |
| EP | 0581020 | 2/1994 |
| EP | 0452623 | 11/1994 |
| EP | 867149 | 9/2000 |
| EP | 0857466 | 6/2002 |
| EP | 1154724 | 8/2003 |
| EP | 1303223 | 8/2005 |
| EP | 2131771 B1 | 11/2010 |
| FR | 776041 | 1/1935 |
| FR | 1501311 | 11/1967 |

(56) References Cited

FOREIGN PATENT DOCUMENTS

| | | |
|---|---|---|
| FR | 2381603 | 9/1978 |
| FR | 2480376 | 10/1981 |
| FR | 2717674 | 9/1995 |
| FR | 2777449 | 10/1999 |
| GB | 206298 | 11/1923 |
| GB | 284014 | 1/1928 |
| GB | 744614 | 2/1956 |
| GB | 1125739 | 8/1968 |
| GB | 1587370 | 4/1981 |
| GB | 2226618 | 7/1990 |
| JP | 9206311 | 8/1997 |
| JP | 2000135230 | 5/2000 |
| JP | 2002045367 | 2/2002 |
| JP | 2002065686 | 3/2002 |
| JP | 2002537057 A | 11/2002 |
| JP | 3118904 | 2/2006 |
| SU | 1419690 | 8/1988 |
| SU | 1600713 | 10/1990 |
| WO | WO 1983/000010 | 1/1983 |
| WO | WO 1995/005127 | 2/1995 |
| WO | WO 2002/009602 | 2/2002 |
| WO | WO 2002/089659 | 11/2002 |
| WO | WO 2004/016187 | 2/2004 |
| WO | WO 2004/075765 | 9/2004 |
| WO | WO 2006/066119 | 6/2006 |
| WO | WO 2006/088452 | 8/2006 |
| WO | WO 2008/124484 | 10/2008 |

OTHER PUBLICATIONS

Estin et al., "Bone Flap Fixation With Tatanium Clamps: A New Technique," Surgical Neurology, 2000, vol. 53, pp. 391-395.

In the United States Patent and Trademark Office, In Re. U.S. Appl. No. 09/910,720, filed Jul. 24, 2004: Office Action dated Jan. 24, 2006.

Japanese Patent Application No. 2010-502284: Official Action dated Oct. 2, 2012, 2 pages.

Lusuardi AG, In Re. EP Patent Application 01933533.0-1265 Filed Jun. 7, 2001, EP Response dated Apr. 8, 2003, 2 pages.

Rapid Resorbable Cranial Clamp brochure for cranial bone flap fixation, Synthes CMF, Jan. 2007, 4 pages.

Summons of Lusuardi, Werther, Dr. Lusuardi AG to Attend Oral Proceedings Pursuant to Rule 115(1) EPC, Regarding EP Patent Application No. 01933533.0-1265, EP Patent No. 1303223, European Patent Office, Jun. 29, 2010, 9 pages.

* cited by examiner

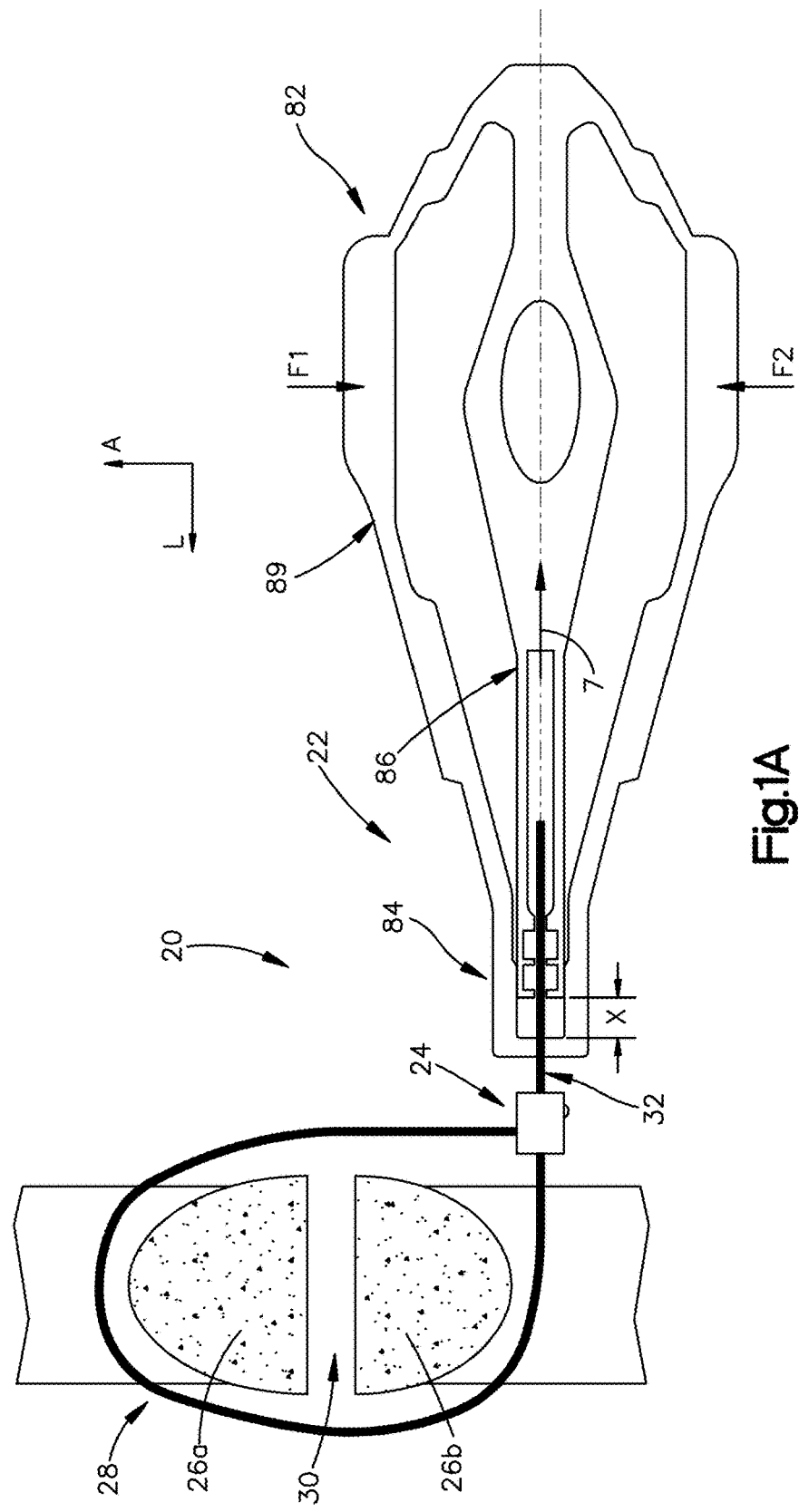

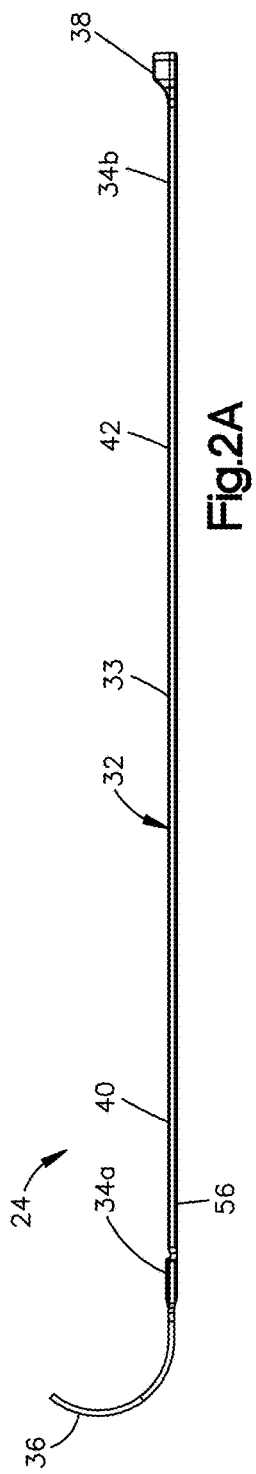
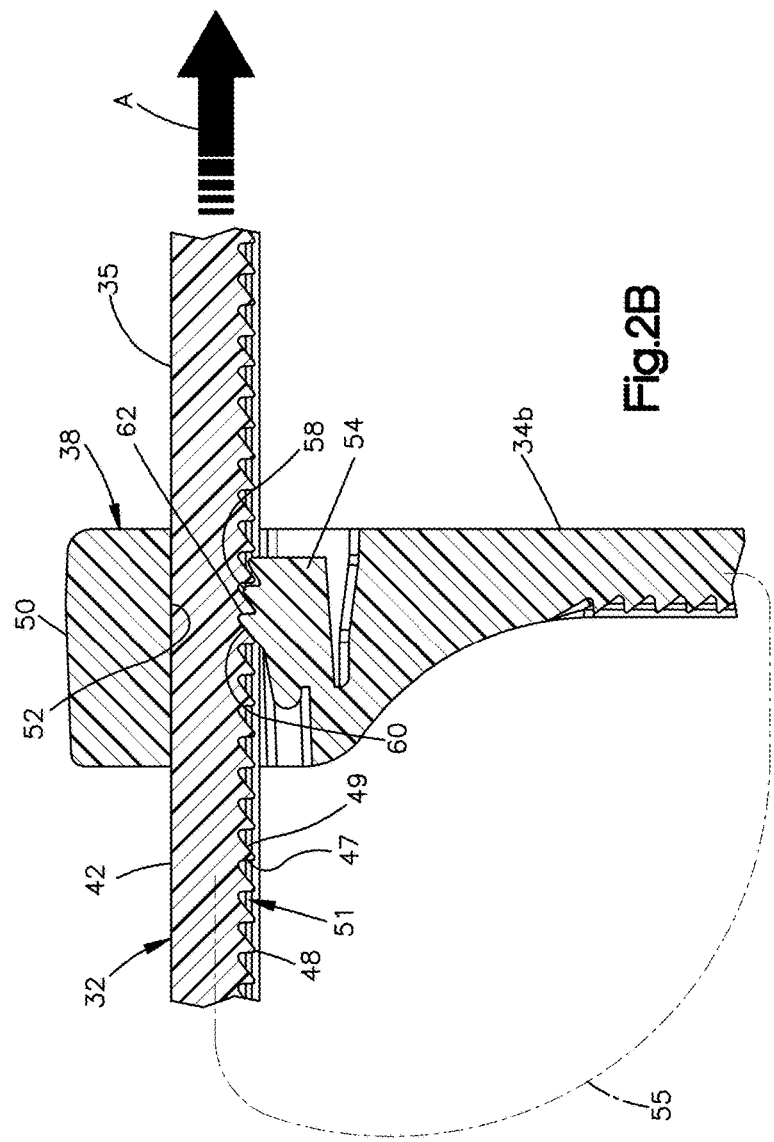
Fig.2A
Fig.2B

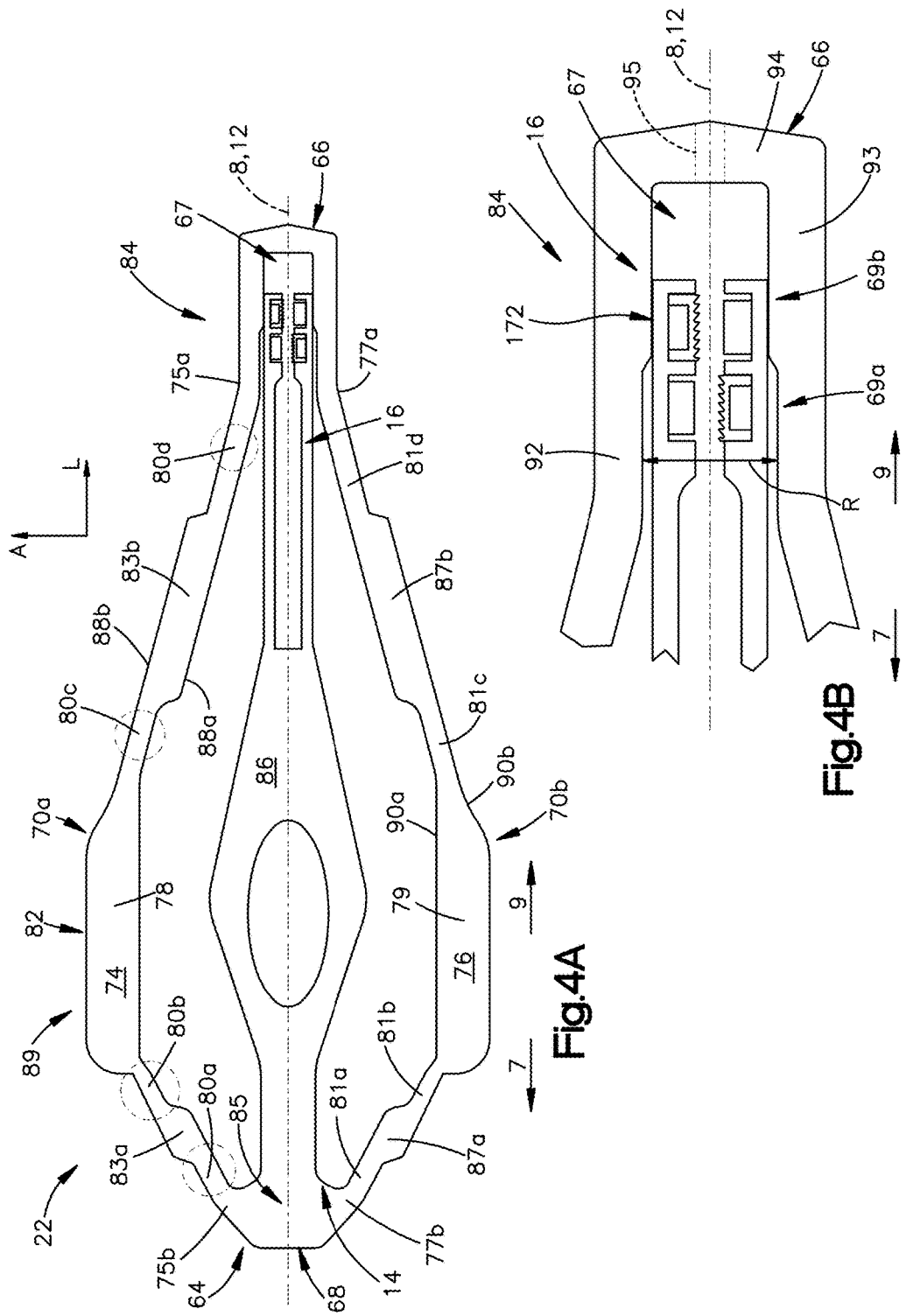

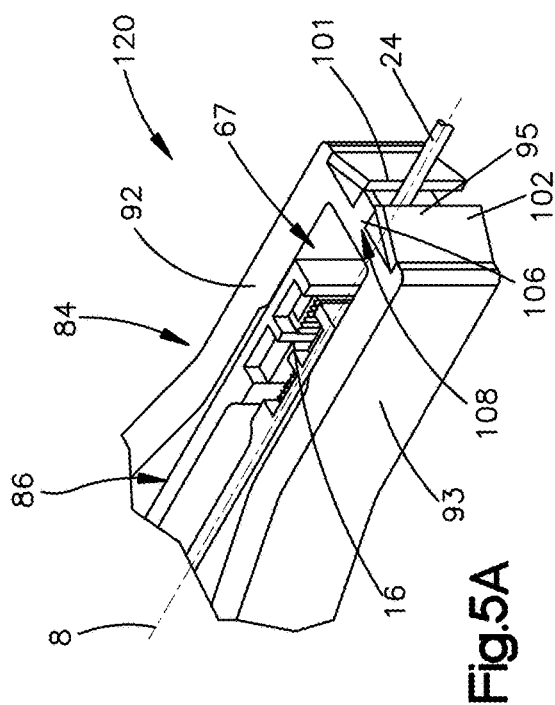
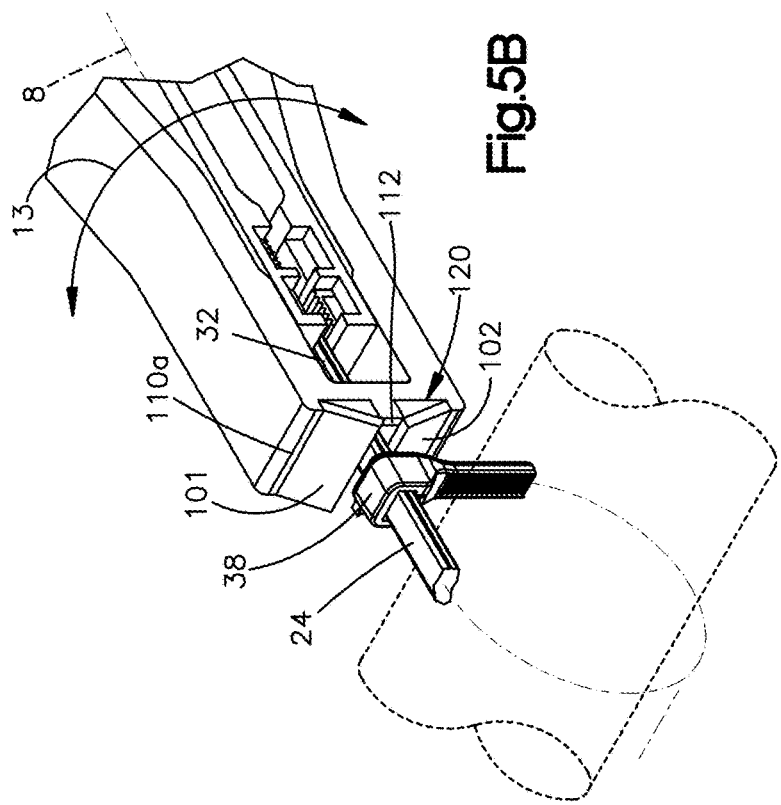
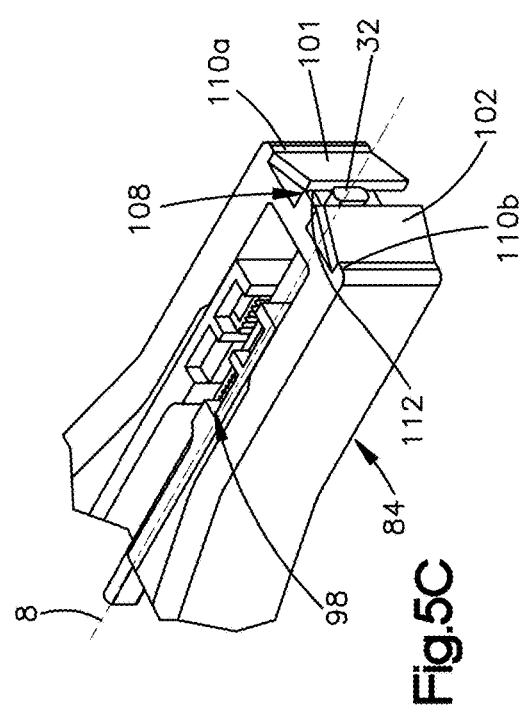

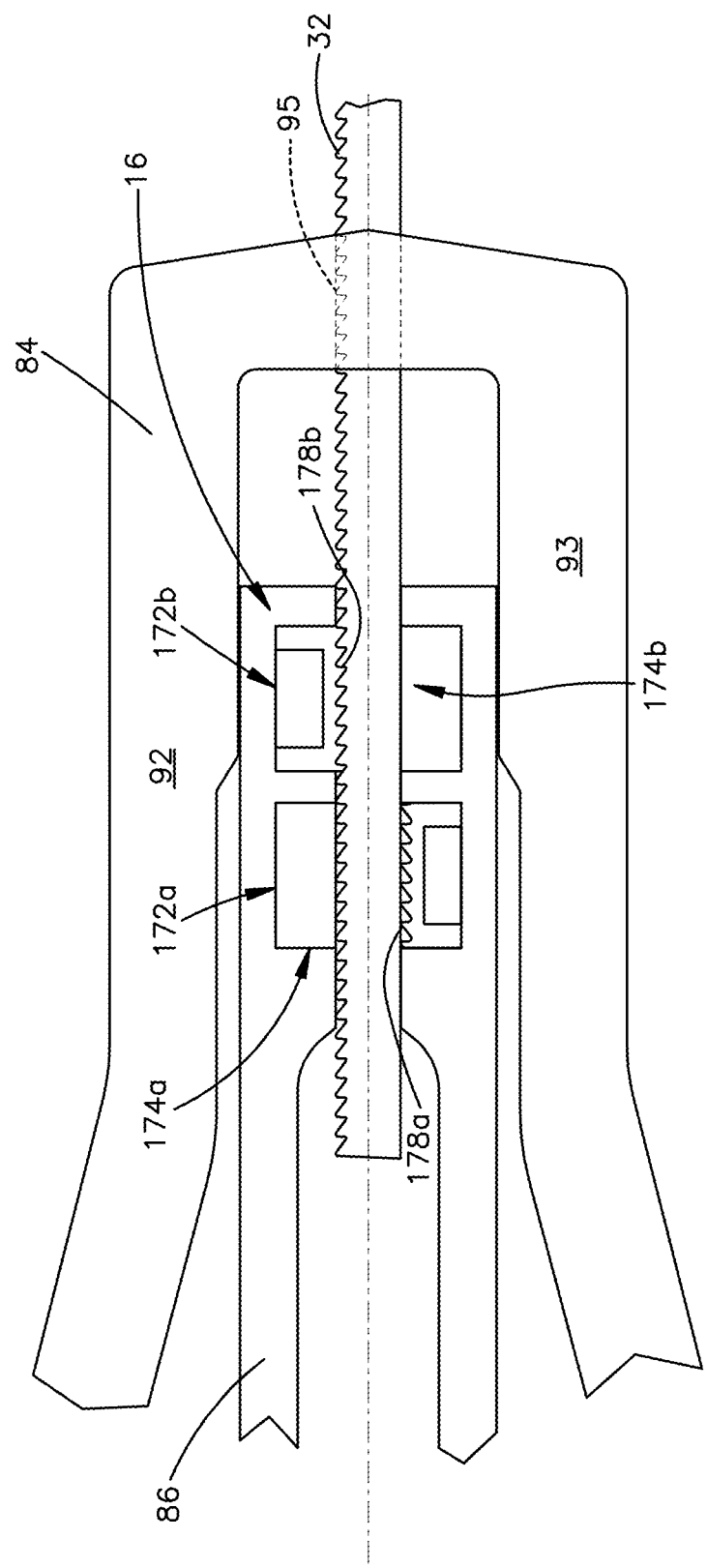

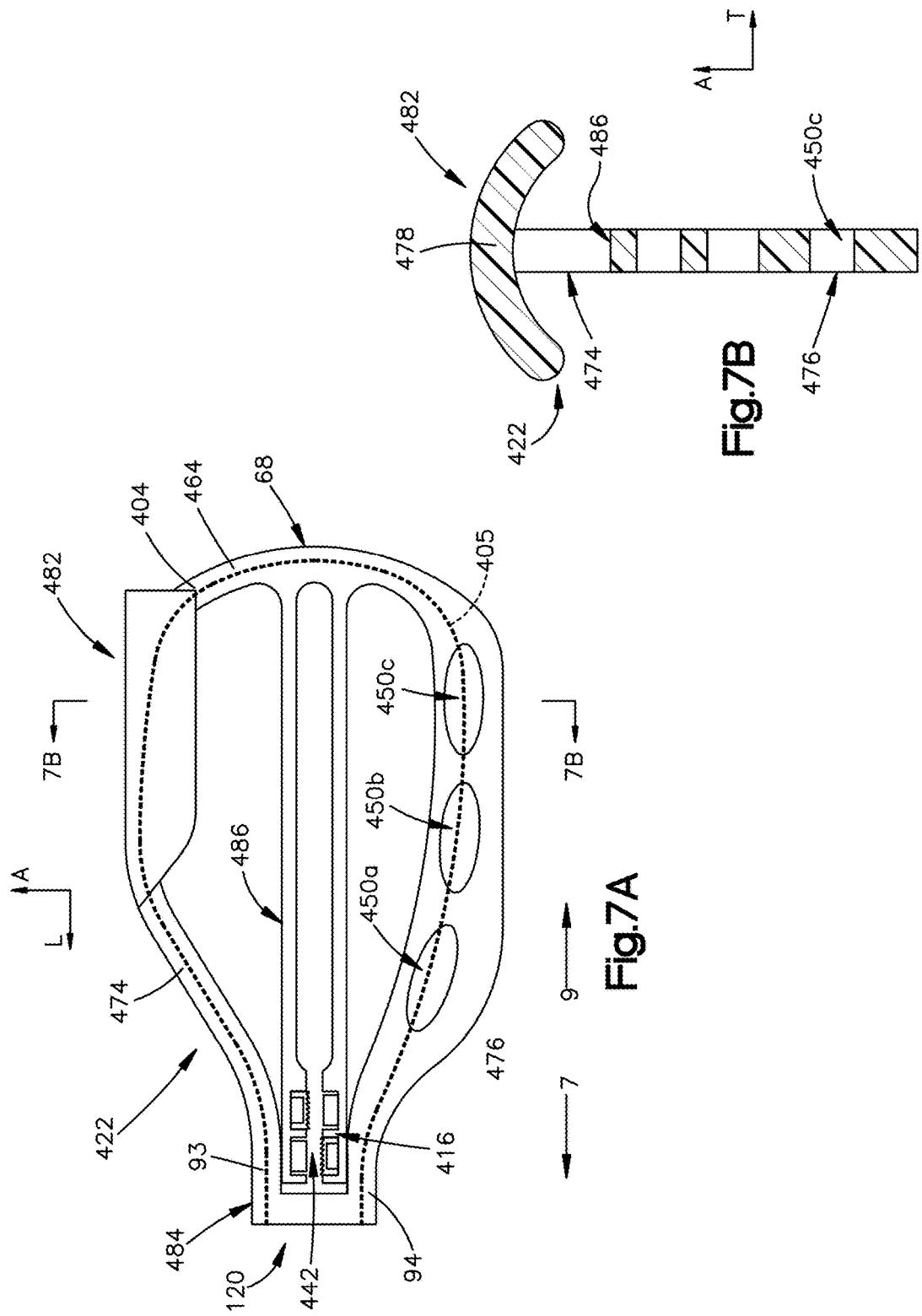

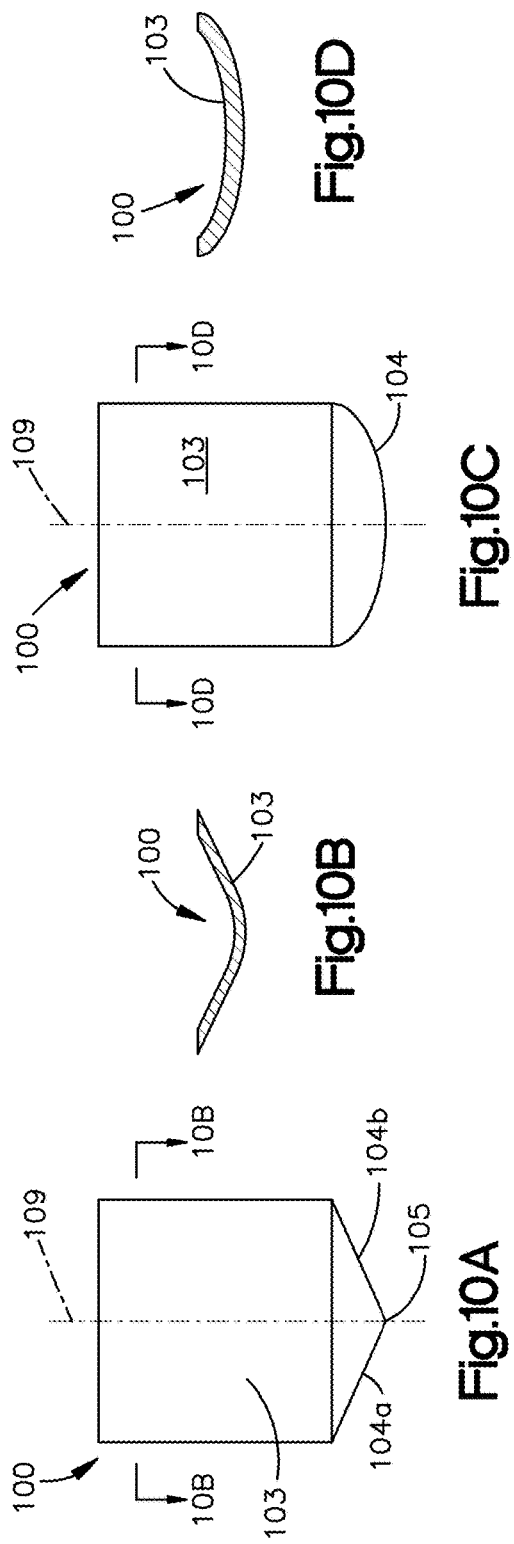

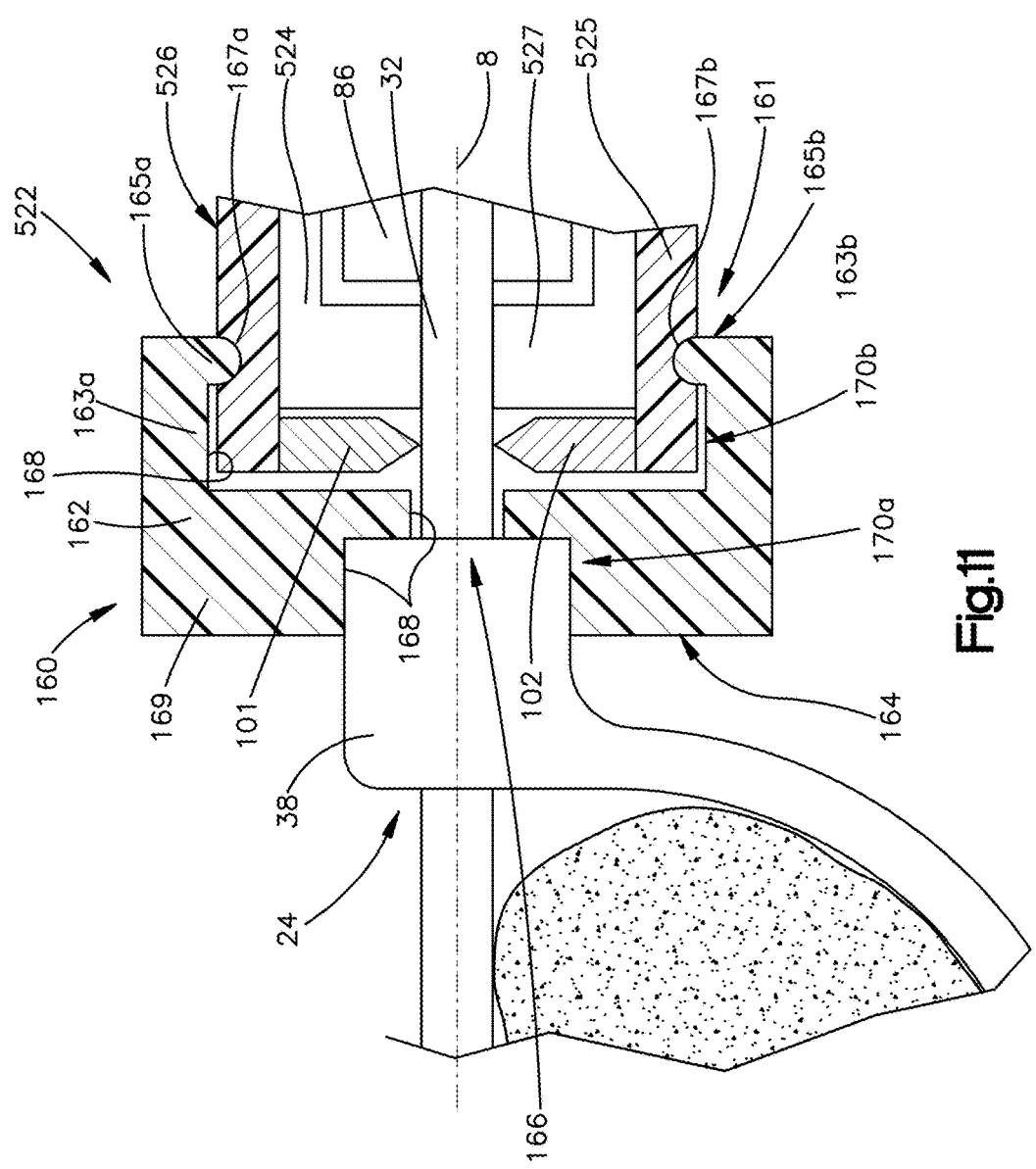

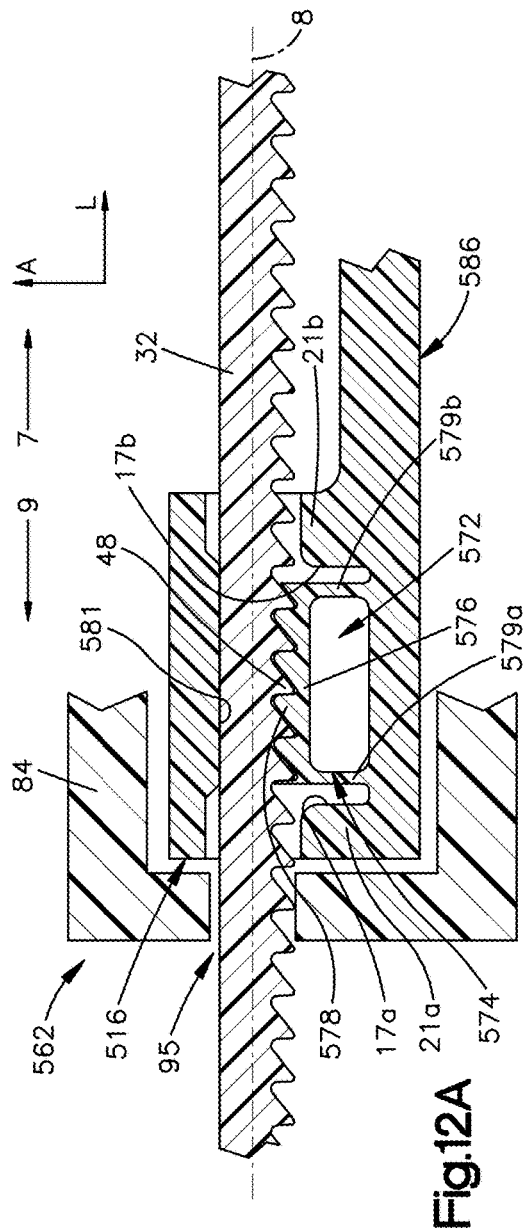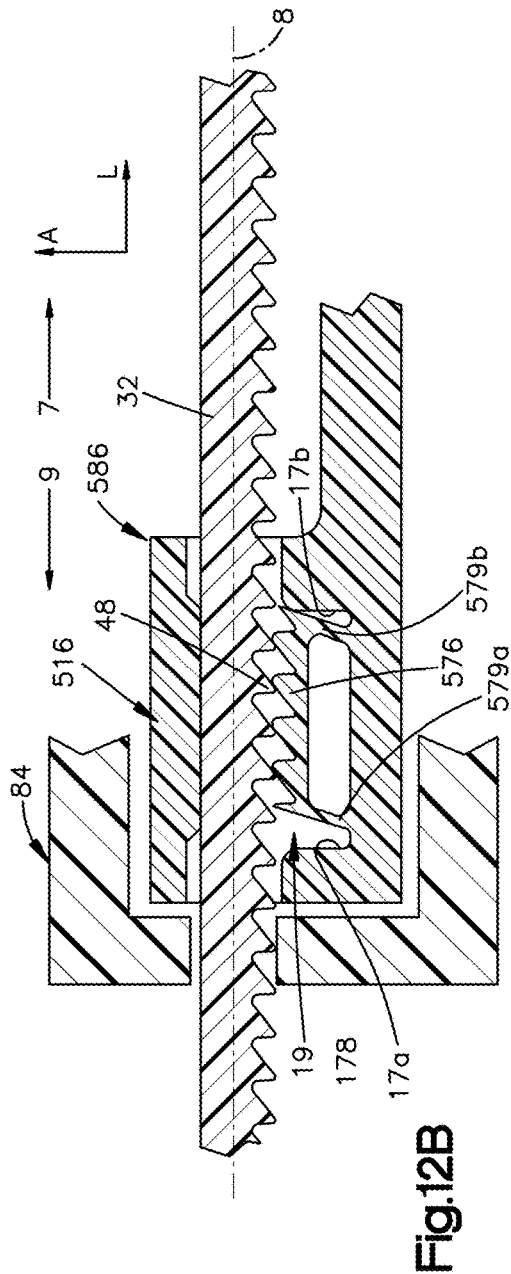
Fig.12A
Fig.12B

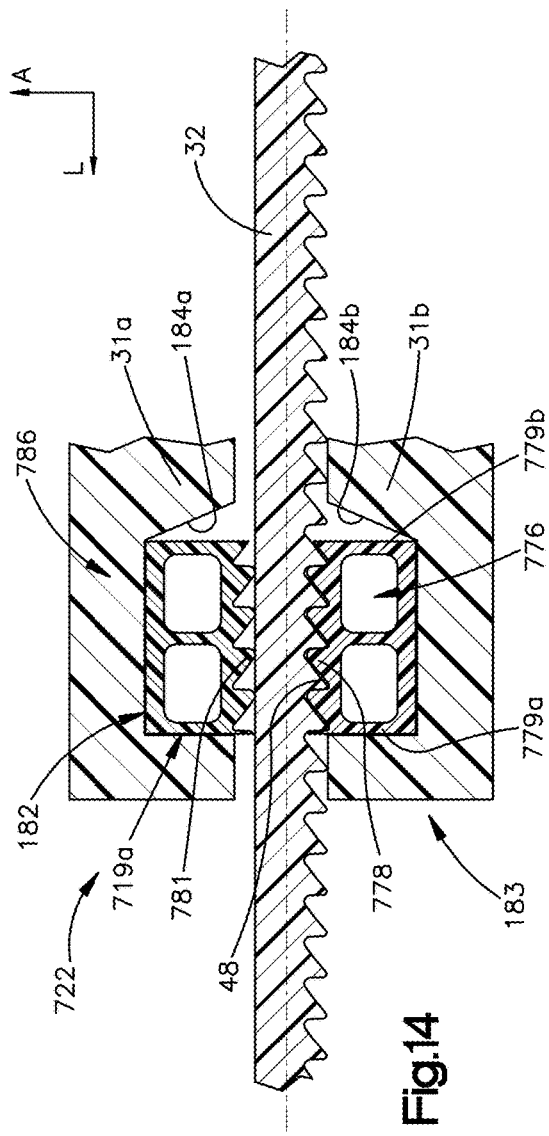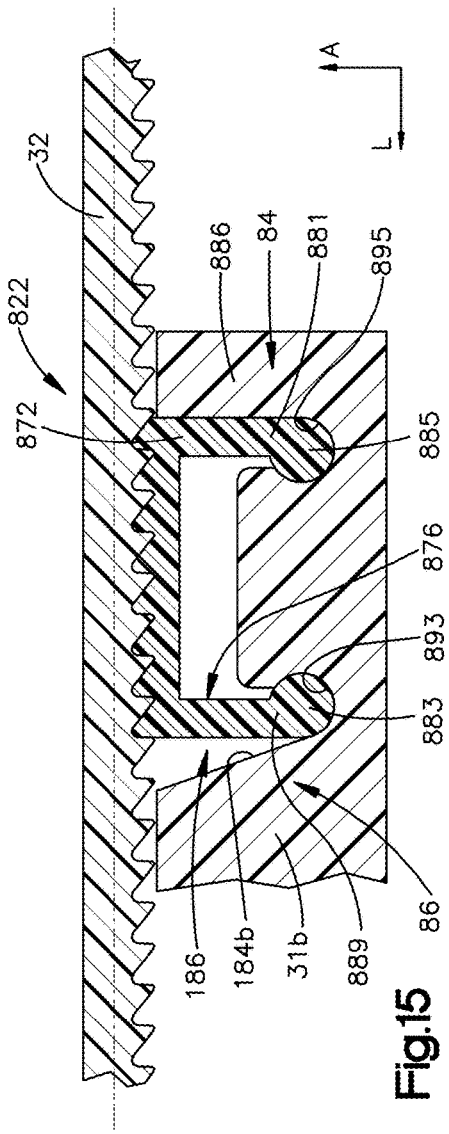

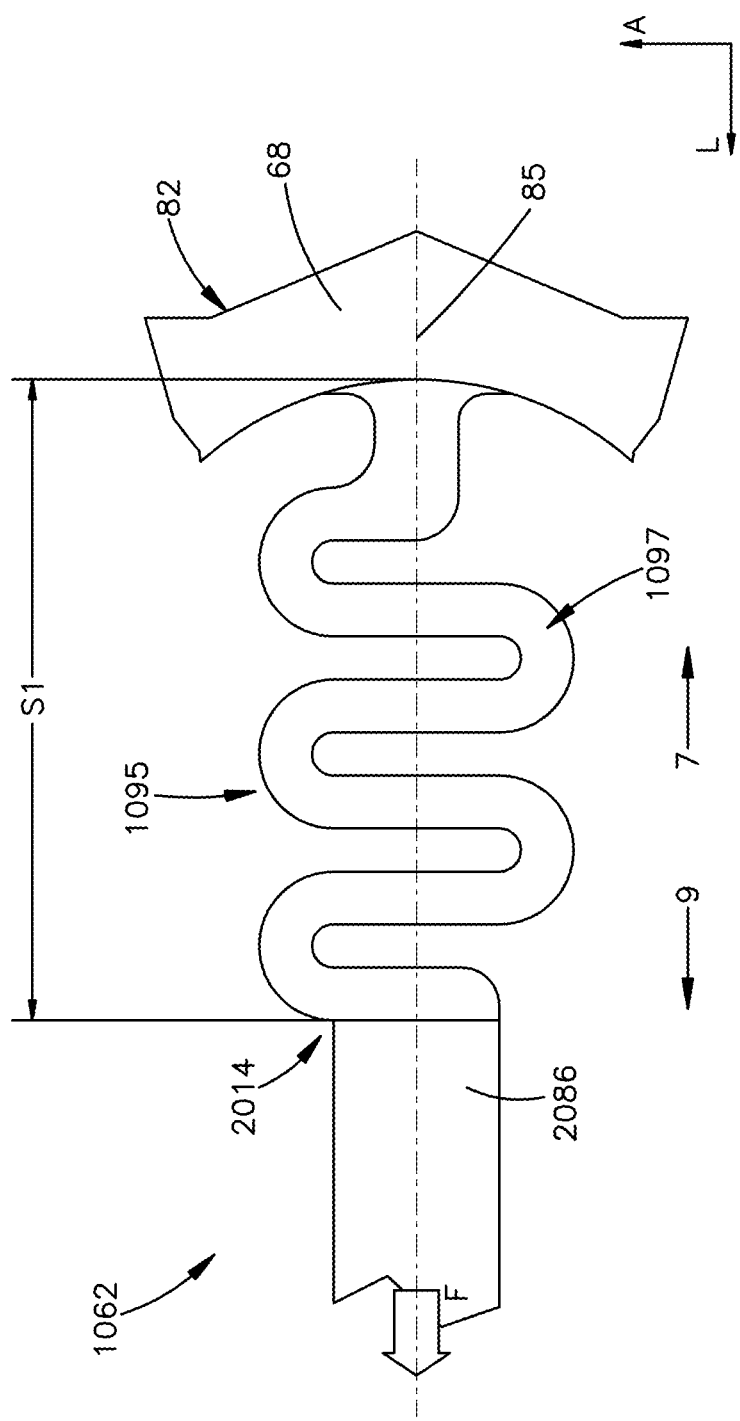

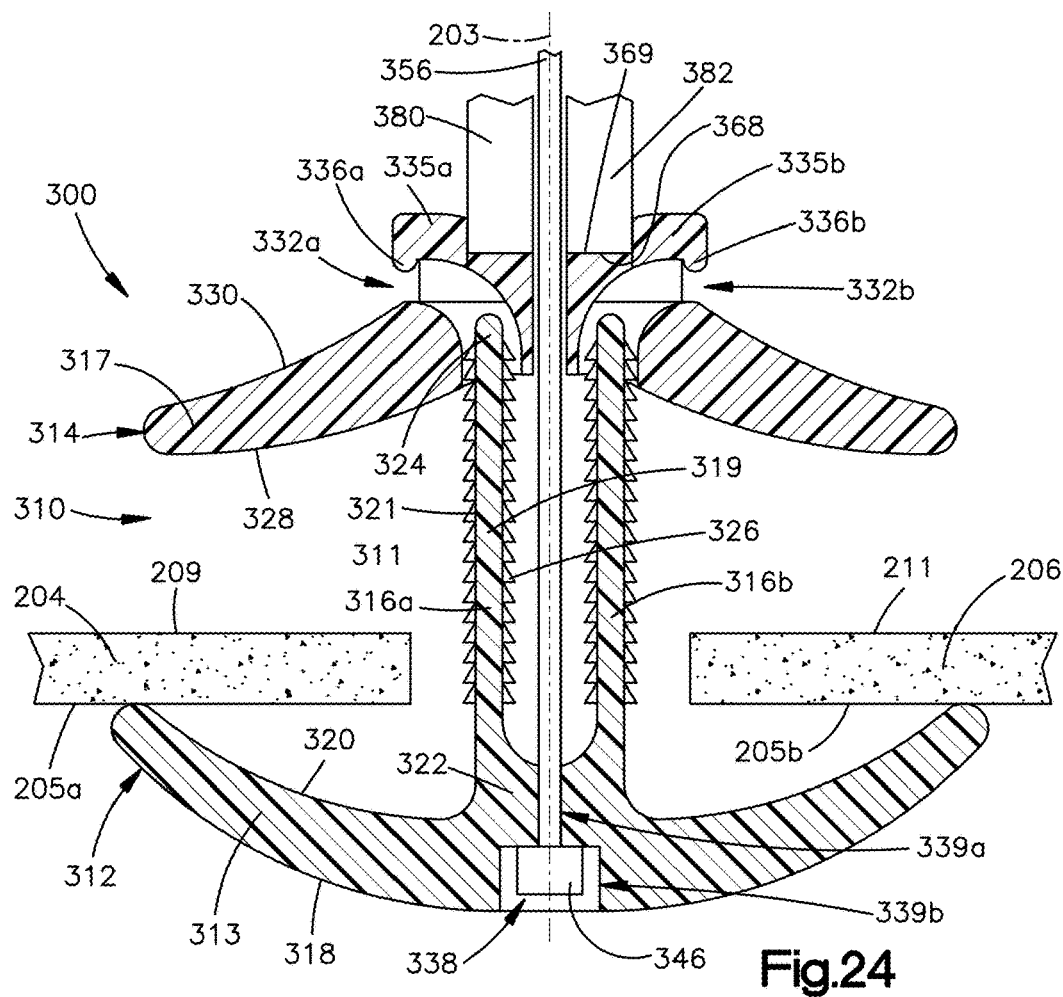
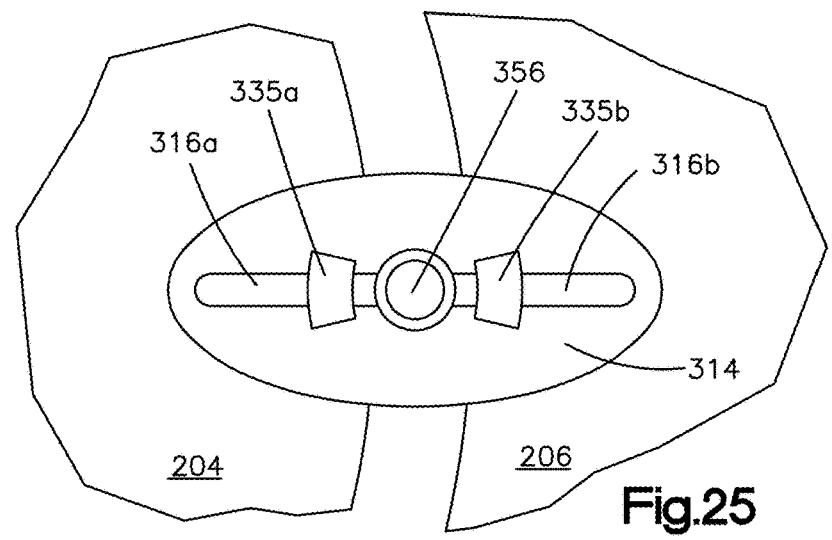

TENSIONING INSTRUMENT AND RELATED BONE FIXATION SYSTEMS AND METHODS

CROSS-REFERENCE TO RELATED APPLICATIONS

This application claims priority to and the benefit of U.S. Provisional Application No. 61/986,434, filed Apr. 30, 2014, the entire disclosure of which is incorporated by reference into this application.

TECHNICAL FIELD

The present disclosure relates to a tensioning instrument, and related bone fixation systems and methods.

BACKGROUND

Bone fixation systems typically maintain bone fragments in position following osteotomy or reduction procedures in order to initiate bone healing. Bone fixation systems include implants, bone fixation members, and instruments. The instruments typically position the implants relative to bone. In some cases, instruments may manipulate the implants into the appropriate position in order to achieve desired restoration of anatomy following a cut or fracture. For instance, a bone fixation member, such as a cable tie, can be wrapped about bone segments. A tensile force applied the cable tie tightens the cable tie around the bone segments attaining the desired reduction. In another example, after a craniotomy, an inner plate positioned inside the cranium next to a bone flap and an outer plate positioned outside cranium hold the bone flap in position. A guide wire attached the inner plate is tensioned, causing the outer and inner plates to clamp the bone flap to the cranium.

SUMMARY

An embodiment of the present disclosure includes an instrument. The instrument includes a bearing member and an actuator spaced from the bearing member in a proximal direction. The instrument also includes a retainer that extends from a location of the actuator toward the bearing member. The retainer is configured to attach to a portion of an implant, wherein the location is spaced from the bearing member a distance in the proximal direction. The actuator includes a flexible portion that is spaced from the retainer in a direction perpendicular to the proximal direction, such that, when a force is applied to the actuator, the actuator deforms so as to increase the distance between the location and the bearing member.

Another embodiment of the present disclosure includes a method for applying tension to an element. The method comprises the step of placing a bearing member against a first portion of the element. The method includes coupling a second portion of the element to a retainer that extends from a location of an actuator that is spaced from the bearing member in a proximal direction, wherein the actuator has a portion that is spaced from the element in a direction that is perpendicular to the proximal direction. The method can include applying an actuation force to the portion of the actuator, causing the actuator to deform and move the location of the actuator and the retainer relative to the bearing member in the proximal direction, thereby applying a tensile force to the second portion of the element.

Another embodiment of the present disclosure includes an instrument. The instrument includes a bearing member an actuator spaced from the bearing member in a proximal direction. The actuator defines a location configured to support a coupling element of an implant, wherein the location of the actuator is spaced from the bearing member a distance in the proximal direction. The actuator includes a flexible portion that is offset with respect to the location of the actuator in a first direction perpendicular to the proximal direction, such that when a force is applied to the actuator, the actuator increases the distance between the location and the bearing member. The coupling element can be attached to or monolithic with the implant.

Another embodiment of the present disclosure is a method for securing an implant to bone, the method comprising the steps of placing a bearing member against a first portion of the implant, the first portion of the implant configured to face a first surface of a bone, the implant including a second portion configured to face a second surface of the bone that is opposite the first surface, and a coupling element that extends from the second portion through the first portion of the implant. The method can include attaching the coupling element to the actuator at a location that is spaced from the bearing member in a proximal direction, such that a flexible portion of actuator is spaced from the coupling element in a direction that is perpendicular to the proximal direction. The method can include applying an actuation force to the flexible portion of the actuator, causing the actuator move the coupling element relative to the bearing member in the proximal direction, thereby urging the second portion of the implant toward the first portion of the implant.

An embodiment of the present disclosure includes a bone fixation system. The bone fixation system includes an implant that includes a first clamp body positionable against a first surface of a bone, and a second clamp body positionable against a second surface of the bone opposite the first surface. The bone fixation system includes an instrument that has a bearing member configured to abut the second clamp body, and an actuator configured to be coupled to the first clamp body such that an elongate member extends from the first clamp body to a location of the actuator that is spaced from the bearing member a distance in the proximal direction. When the actuator is coupled to the first clamp body, a flexible portion of the actuator is spaced from the elongate member in a direction perpendicular to the proximal direction, such that, when a force is applied to the flexible portion, the flexible portion of the actuator deforms so as to increase the distance between the location and the bearing member.

BRIEF DESCRIPTION OF THE DRAWINGS

The foregoing summary, as well as the following detailed description of illustrative embodiments of the tensioning instrument and related bone fixation systems of the present application, will be better understood when read in conjunction with the appended drawings. It should be understood, however, that the application is not limited to the precise schematics and arrangements shown. In the drawings:

FIG. 1A is a plan view of an instrument according to an embodiment of the present disclosure, showing the instrument in a first configuration holding a bone fixation member around an underlying bone;

FIG. 2A is a side view of a bone fixation member including a body and a locking member;

FIG. 2B is a detailed sectional view of a portion of the bone fixation member illustrated in FIG. 2A, showing the body inserted through the locking member so as to secure the bone fixation member about the underlying bone;

FIG. 4A is a plan view of the instrument shown in FIGS. 1A and 1B;

FIG. 4B is a detailed view of a portion of the instrument shown in FIG. 4A.

FIGS. 5A through 5C are perspective views of the instrument shown in FIGS. 1A, 1B and 4A-through 4D;

FIGS. 6A and 6B are partial plans views of the instrument shown in FIGS. 1A, 1B and 4A-through 4D, showing a locking assembly configured to capture a portion of a bone fixation member;

FIG. 7A is a plan view of an instrument according to another embodiment of the present disclosure;

FIG. 7B is a cross-sectional view of the instrument taken along lines 7B-7B in FIG. 7A;

FIGS. 10A through 10F illustrate embodiments of cutting blades used with the instrument shown in FIGS. 8A and 8B;

FIG. 11 is a sectional view of a portion an instrument according to another embodiment of the present disclosure;

FIG. 12A is a sectional view of a portion of an instrument according to another embodiment of the present disclosure, showing the instrument holding a bone fixation member in a locked configuration;

FIG. 12B is a sectional view of the instrument shown in FIG. 12A, showing the instrument holding the bone fixation member in an unlocked configuration;

FIG. 14 is a sectional view of a portion of an instrument according to another embodiment of the present disclosure;

FIG. 15 is a sectional view of a portion of an instrument according to another embodiment of the present disclosure;

FIG. 18B is a plan view of a portion of an instrument according to another embodiment of the present disclosure;

FIG. 24 is a detailed side view of a portion of the bone fixation system shown in FIG. 23; and FIG. 25 is a top view of the bone fixation system shown in FIG. 23, showing a portion of the instrument removed.

DETAILED DESCRIPTION OF ILLUSTRATIVE EMBODIMENTS

Figure 1B:
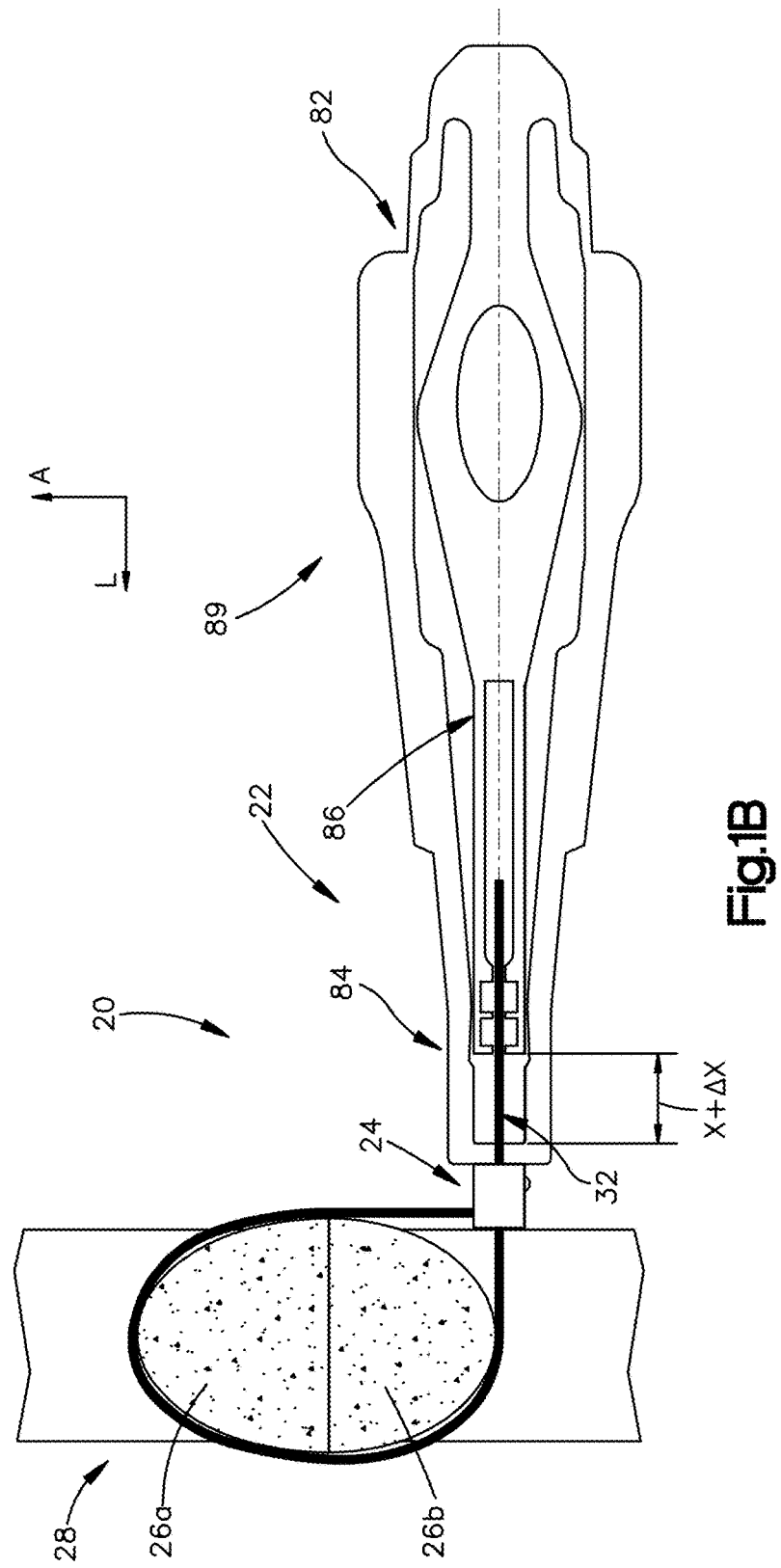
FIG. 1B is a plan view of the instrument shown in FIG. 1A, showing the instrument in a second configuration with the bone fixation member tightened about the underlying bone.

Certain terminology is used in the following description for convenience only and is not limiting. The words "right", "left", "lower" and "upper" designate directions in the drawings to which reference is made. The words, "anterior", "posterior", "superior", "inferior" and related words and/or phrases designate preferred positions and orientations in the human body to which reference is made and are not meant to be limiting. Further, the description refers to a bone fixation system and related components and instruments and/or portions of same that include a "proximal end" and a "distal end." Thus, a "proximal direction" or "proximally" refers to a direction that is oriented generally from the distal end toward the proximal end. A "distal direction" or "distally" refers to a direction that is oriented generally from the proximal end toward the distal end. The components of bone fixation system of the present disclosure are also described herein as extending along a longitudinal direction "L" and a lateral direction "A", and transversely along a transverse direction "T". Unless otherwise specified herein, the terms "longitudinal," "transverse," and "lateral" are used to describe the orthogonal directional components of various bone fixation system components and component axes.

The present disclosure relates to bone fixation systems that include a tensioning instrument configured to apply a tensile force to a portion of an implant, such as a bone fixation member 24 as shown in FIGS. 1A and 1B, or bone fixation implants 210 and 310 as shown in FIGS. 19-25. The tensioning instrument is configured such that when the instrument is coupled to the implant, a portion of the instrument can be displaced so as to apply a tensile force to the implant in order to secure the implant to bone, as will be further detailed below. An implant as used here includes a bone fixation member, clamping device, bone plate, anchor, or any other device configured for implantation into a patient.

Turning to FIGS. 1A and 1B, a bone fixation system 20 includes an instrument 22 and at least one implant 24, such as a plurality of implants 24. The implants 24 are configured to secure the first and second bone segments 26a and 26b of a target bone 28, such as a sternum, separated at an osteotomy location 30 together in a compressed approximated position. The instrument 22 can include an actuator 82 and a bearing member 84 that extends from the actuator 82 along the longitudinal direction L. An elongate member, such as a retainer 86, can extend from a portion of the actuator 82 toward the bearing member 84 in the longitudinal direction L. The actuator 82 can include a flexible portion 89 that is spaced from the retainer 86 such that when a force is applied to the actuator 82 toward the retainer 86 in a direction perpendicular to the longitudinal direction L, at least a portion of the actuator 82 is displaced along the longitudinal direction L, thereby displacing retainer 86 relative to the bearing member 84. Displacement of the retainer 86 applies a force to an implant 24 when the retainer 86 is attached to the implant 24. In accordance with the illustrated embodiment, the instrument 22 can have a first, or initial configuration (FIG. 1A) wherein the implant 24 is received by the instrument 22 and surrounds the bone segments 26a and 26b, and a second or actuated configuration (FIG. 1B) wherein the retainer 86 has been displaced so that the desired tensile force is applied to the implant 24 and the implant 24 to be tightened about the bone segments 26a and 26b to reduce size of the osteotomy location 30. In accordance with the illustrated embodiment, the implant 24 may be a bone fixation member, such as a cable tie.

Figure 3:
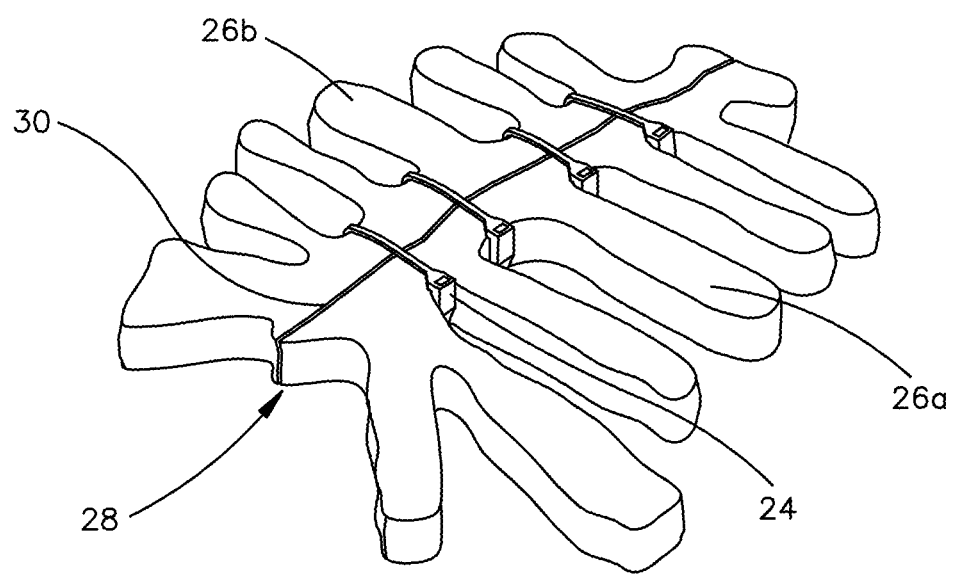
FIG. 3 is a perspective view of a plurality of the bone fixation members illustrated in FIG. 2A, showing the bone fixation members tightened about a target bone.

Referring to FIGS. 2A-3, each bone fixation member 24 can include a flexible member, such as strap 32 that defines a strap body 33 and has first end 34a and a second end 34b opposite the first end 34a along the length of the strap 32, a needle tip 36 that extends from the first end 34a, and a locking mechanism 38 that extends from the second end 34b. The strap 32 can be made from any suitable biocompatible material as desired, such as PEEK.

Each bone fixation member 24 can further include a first initiation region 40 that extends from the first end 34a toward the second end 34b along a portion of a length of the strap 32 (for instance, approximately ⅓ the length of the strap 32) and a second locking region 42 that extends between the first initiation region 40 and the second end 34b. In accordance with the illustrated embodiment, the second locking region 42 extends from the first initiation region 40 to the second end 34b. The second end 34b may define a support surface. The bearing member 84 can abut the support surface. The first initiation region 40 can include a plurality of small protrusions that extend out from the strap body 33 and alternate with recessed regions disposed between adjacent protrusions. Alternatively, the initiation region 40 can be substantially smooth and devoid of protrusions or teeth. The second locking region 42 can include a plurality of locking teeth 48 that extend out from the strap body 33 a distance greater than the protrusions and are separated by recessed regions 51 disposed between adjacent locking teeth. It should be appreciated that the locking region 42 can extend along any portion up to all of the strap body 33 as desired.

The locking mechanism 38 includes a housing 50 a strap receiving slot 52 that extends through the housing 50 and is configured to receive the first end 34a of the strap 32. In accordance with the illustrated embodiment, the first end 34a is inserted through the slot 52 to define a loop 55 disposed along a side of the locking mechanism 38. The loop 55 encircles the target bone 28. The locking mechanism 38 is configured to allow the strap 32 to translate uni-directionally through the slot 52 along the direction of Arrow A so as to reduce the size of the loop 55 about the first and second segments 26a and 26b of the target bone 28. For instance, the needle tip 36 can be inserted through the slot 52 and subsequently removed, for instance by cutting a neck 56 of the strap body 33 that defines reduced thickness at a location adjacent the needle tip 36, such that the strap 32 remains in the slot 52. In accordance with the illustrated embodiment, the locking mechanism 38 includes a locking member such as a tongue 54 that is connected to the housing 50 and includes at least one complementary tooth such as a plurality of locking teeth 58 that extend into the slot 52. The locking teeth 58 define a beveled leading edge 60 that is configured to cam over complementary beveled leading edges 49 of the locking teeth 48 when the strap 32 is translated through the slot 52 along the direction of Arrow A. The locking teeth 58 and 48 further define trailing edges 62 and 47 that are sloped less than the beveled leading edges 60, such that the trailing edges 62 and 47 engage to prevent the strap 32 from translating through the slot 52 along the direction opposite Arrow A, which would increase the size of the loop 55.

During operation, the strap 32 is wrapped around the first and second segments 26a and 26b of the target bone 28, and the needle tip 36 is inserted through the slot 52 and pulled through the slot 52 so as to cause the strap 32 to subsequently translate through the slot 52. The needle tip 36 can be removed from the strap 32, and the strap 32 can then be further pulled, for instance manually, through the slot 52. As the strap 32 is translated through the locking mechanism 38 along the direction of Arrow A, the small protrusions of the initiation region 40 can slide through the slot 52 without engaging the locking teeth 58 of the locking mechanism 38. As the locking region 42 of the strap 32 is translated through the slot 52 along the direction of Arrow A, the locking teeth 48 and 58 can engage to prevent the tension that is induced in the strap 32 from causing the strap 32 to back out of the slot 52 along a direction opposite Arrow A. For instance, as the strap 32 translates through the locking mechanism 38 along the direction of Arrow A, the size of the loop 55 about the target bone 28 decreases until the desired tension has been induced in the strap 32.

Referring now to FIGS. 4A-4D, the tensioning instrument 22 includes an instrument body 64 that defines a front or distal end 66, an opposed rear or proximal end 68 spaced from the front end 66 in the longitudinal direction L, and opposed sides 70a, 70b that are spaced along a lateral direction A that is substantially perpendicular to the longitudinal direction L. The distal end 66 can define the bearing member 84 such that actuator 82 extends from the proximal end 68 to the bearing member 84. In accordance with the illustrated embodiment, the body 64 is elongate in the longitudinal direction L to define a length, has a thickness that extends along the transverse direction T and a width that extends along the lateral direction A. It should be appreciated that the longitudinal direction L may be referred to as a first direction and the lateral direction A may be referred to as the second direction. Alternatively, the longitudinal direction L may be referred to as a second direction and the lateral direction A may be referred to as the first direction. The instrument body 64 can be made of any material suitable for medical use. The material can be a metallic material, e.g. stainless steel, titanium, a titanium based alloy, a polymeric material, e.g. such as PEEK, or a combination of a metallic and a polymeric materials.

Figure 4C:
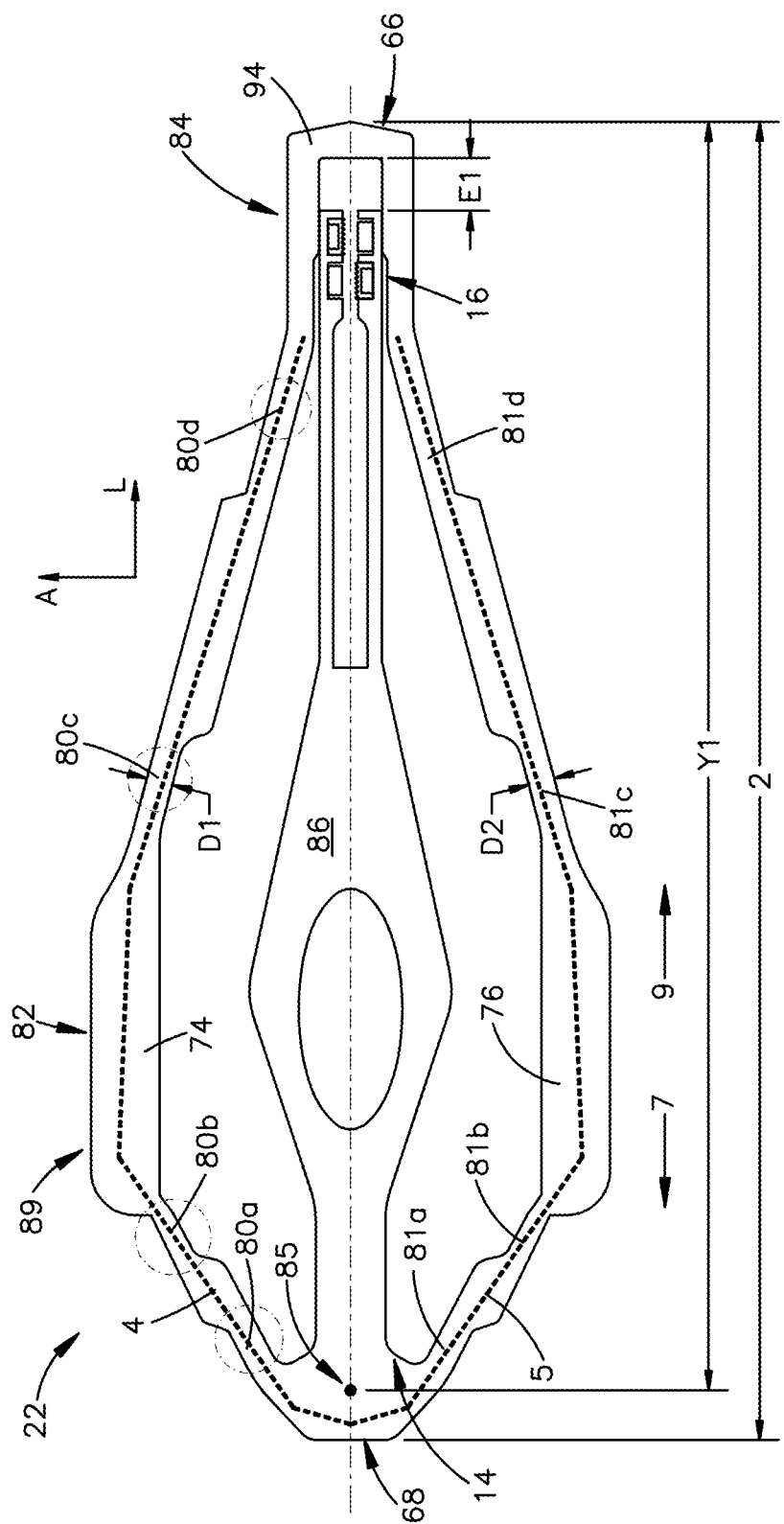
FIGS. 4C and 4D are plan views of the instrument shown in FIG. 4A in a first configuration and a second actuated configuration, respectively.
Figure 4D:
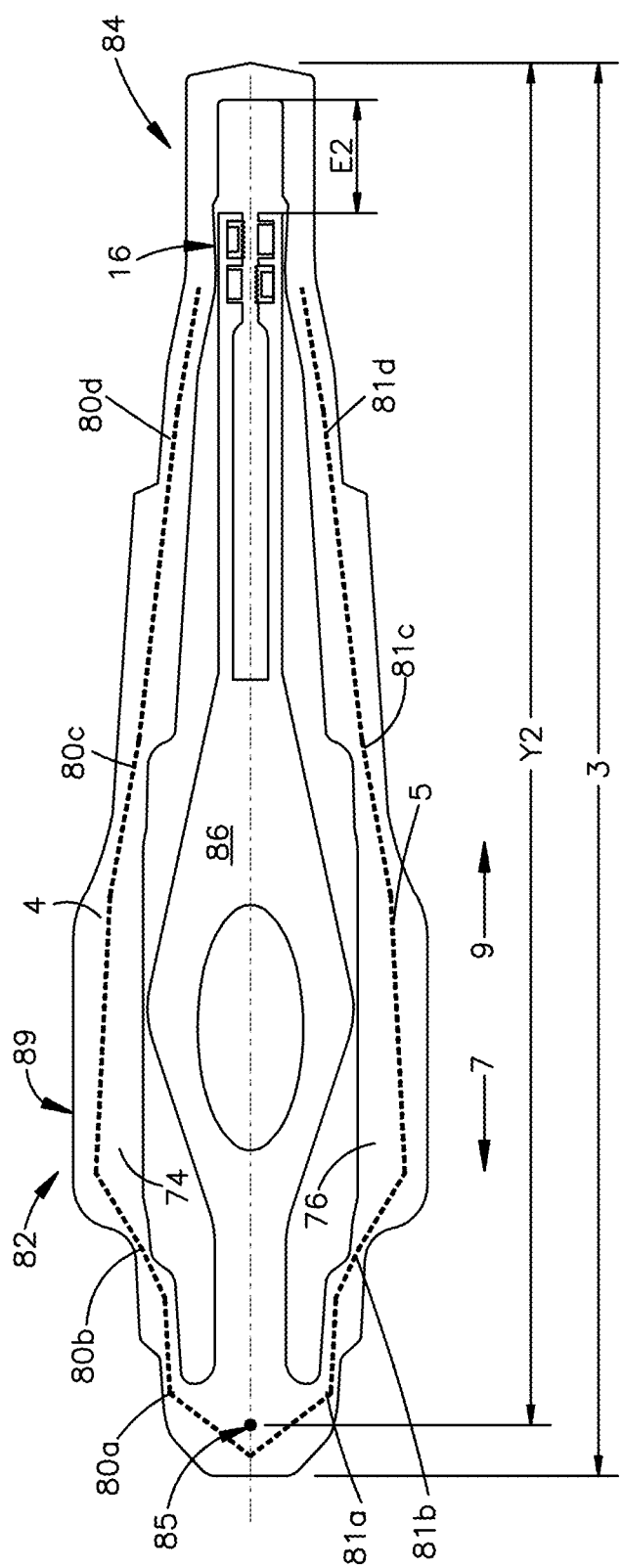

Turning to FIGS. 1A, 4C, and 4D, the instrument 22 includes the actuator 82 and the bearing member 84. Further, the instrument 22 is configured such that the retainer 86 extends from a select location 85 of the actuator 82. For instance, the retainer 86 can be attached to the actuator 82 at the select location 85 or monolithic with the actuator 82 at the select location 85. The select location 85 is spaced a distance from the bearing member 84. The retainer 86 is configured to move relative to the bearing member 84 in the longitudinal direction L, for instance in a proximal direction 7, so as to apply a tensile force along the retainer 86 when the retainer 86 is attached to the implant 24. In accordance with the illustrated embodiment, the instrument 22 is configured such that when opposing compressive forces F1 and F2 (FIG. 1A) are applied to the actuator 82 along the lateral direction A, the actuator 82 is deformed toward the retainer 86. Deformation of the actuator 82 toward the retainer 86 in the lateral direction A moves the retainer 86 away from the bearing member 84 in the proximal direction 7, increasing the distance between the location 85 and the bearing member 84 as further detailed below. Movement of the retainer 86 in the proximal direction 7 pulls the implant 24 in the proximal direction 7. For instance, when the actuator 82 is in the first configuration (FIG. 4C), the retainer 86 is in a first position relative to the bearing member 84. When actuator 82 is in the second or actuated configuration (FIG. 4D), the retainer 86 has been displaced to a second position relative to bearing member 84 that is spaced from first position in the longitudinal direction L, for instance the proximal direction 7.

Turning to FIG. 1B, the bearing member 84 is configured to be placed against a first portion of the implant 24, such as the locking mechanism 38, such that a second portion of the implant 24, such as the strap 32, can be inserted into the retainer 86. The bearing member 84 can maintain the first portion of the implant 24 in position relative to the retainer 86 as the retainer 86 moves in the proximal direction 7. In accordance with the illustrated embodiment, when the instrument 22 is positioned so that the bearing member 84 abuts surface 34b and the retainer 86 is attached to strap 32, actuation of the actuator 82 causes the attached portion of the strap 32 to advance through the locking mechanism 38. As further detailed below, application of the actuation forces F1 and F2 causes the actuator 82 to deform, thereby displacing the retainer. The actuator 82 is configured such that application of the forces F1 and F2 deforms the actuator 82 to an extent that is that is sufficient overcome any frictional forces between the strap 32 and locking mechanism 38.

Turning to FIG. 4B, the bearing member 84 defines a receptacle 67 configured to receive a portion of the retainer 86, and a channel 95 configured to receive therethrough a portion of the implant 24 that is connected to the retainer 86. The bearing member 84, or distal end 66 of the instrument body 64, defines opposed walls 92 and 93 spaced apart along the lateral direction A and a distal wall 94 that extends between the walls 92 and 93. The walls 92 and 93 extend from the actuator 82 toward the distal wall 94. The walls 92, 93 and 94 define an inner surface (not numbered) that at least partially defines the receptacle 67. The receptacle 67 has a thickness R that extends from the inner surface of wall 92 to the inner surface of the wall 93 along the lateral direction A. The receptacle 97 has a proximal portion 69a and a distal portion 69b that is disposed relative to the proximal portion 69a toward the distal end 66 in the distal direction 9. The thickness R can taper toward the distal wall 94 such that the thickness R at the distal portion 69b is less than the thickness R at the proximal portion 69a. The thickness R of the distal portion 69b is slightly greater than the thickness of a distal end 16 of the retainer 86 such that portion of the walls 92 and 93 that define the distal portion 69b of the receptacle 67 provide a frictional fit with the distal end 16 of the retainer 86. The frictional fit between the retainer 86 and bearing member 84 improves instrument stability when the instrument 22 actuated and is cutting the received bone fixation member 24 as further detailed below. As discussed above, the channel 95 extends through the distal wall 94 in the longitudinal direction L. The channel 95 is sized and configured to receive the strap 32 (FIG. 2A) of the bone fixation member 24 therethrough. The strap 32 can extend through the channel 95 and may be retained by the retainer 86 as further detailed below.

Continuing with FIGS. 4A and 4B, the retainer 86 can extend from the select location 85 of the actuator 82 toward the bearing member 84. In accordance with the illustrated embodiment, the retainer 86 is elongate along a retainer axis 12 and includes a retainer proximal end 14 and a retainer distal end 16 spaced from the retainer proximal end 14 along the retainer axis 12. The retainer proximal end 14 may be coupled to the instrument body 64 opposite the bearing member 84 such that retainer 86 extends from the proximal end 68 of the instrument body 64 toward bearing member 84. Alternatively, the retainer proximal end 14 may be monolithic with the actuator 82. The distal end 16 of the retainer 86 can be aligned with the bearing member 84 when the instrument 22 is in the first or initial configuration. However, the retainer 86 can be configured such that that the distal end 16 of the retainer 86 is not aligned with bearing member 84 when the instrument 22 is in the initial configuration. The distal end 16 of the retainer 86 carries a locking assembly 172a and/or 172b configured to receive and attach to the implant 24, as will be further detailed below.

The actuator 82 is configured to deform in response to application of the compressive forces F1 and F2 so as to displace the retainer 86 along the longitudinal direction L. As discussed above, the actuator 82 includes the flexible portion 89. The flexible portion 89 can include a first actuation member 74 and a second actuation member 76 opposed to the first actuation member 74. The first and second actuation member 74 and 76 can be spaced apart from the retainer 86 in the lateral direction A. In accordance, with the illustrated embodiment, the first and second actuation members 74 and 76 can be configured as first and second arms, respective, configured to flex or bend at specific locations along each actuation member when a compressive force F1, F2 are applied to flexible portion 89 of the actuator 82. The first actuation member 74 includes a front end 75a disposed adjacent to the bearing member 84, a rear end 75b disposed at the proximal end 68 of the instrument 22, and a first support member 78 disposed between the front and rear ends 75a and 75b. The first actuation member 74 is elongate and extends along a first actuator axis 4 (FIG. 4C). The first actuation member 74 defines an inner surface 88a that faces the retainer 86, and an opposed outer surface 88b. The second actuation member 76 also includes a front end 77a adjacent to the bearing member 84, a rear end 77b disposed at the proximal end 68 of the instrument 22, and a second support member 79 disposed between the front and rear ends 77a and 77b. The second actuation member 76 is elongate and extends along a second actuator axis 5 (FIG. 4C). The second actuation member 76 defines an inner surface 90a that faces the retainer 86, and an opposed outer surface 90b.

Turning to FIG. 4A, the actuator 82 can include at least one articulation, such as a plurality of articulations 80a-80d and 81a-81d, respectively. In accordance with the illustrated embodiment, the first and second actuation members 74 and 76 each define at least one articulation, such as a plurality of articulations 80a-80d and 81a-81d, respectively. In this regard, the first and second actuation members 74 and 76 may be referred to as articulating actuators that are configured to articulate when compressive forces F1 and F2 are applied to the flexible portion 89 of the actuator 82. The first actuation member 74 can include a first plurality of articulations 80a, 80b, 80c, and 80d. A first pair of articulations 80a and 80b are located between the rear end 75b of the first actuation member 74 and the support member 78, and a second pair of articulations 80c and 80d are located between the support member 78 and the front end 75a of the first actuation member 74. The first actuation member 74 also includes first and additional support members 83a and 83b disposed between each articulation in the first and second pairs of articulations.

Continuing with FIG. 4A, the second actuation member 76 includes a second plurality of articulations 81a, 81b, 81c, and 81d, and one or more support members 87a, 87b. Articulations 81a and 81b are located between the rear end 77b of the second actuation member 76 and the support member 79. Articulations 81c and 81d are located between the support member 79 and front end 77a of the second actuation member 76. As illustrated, the first actuation member articulations 80a, 80b, 80c, 80d may be aligned with the second actuation member articulations 81a, 81b, 81c, and 81d along the lateral direction A. The second actuation member 76 also includes first and second support members 87a and 87b disposed between each articulation in the respective first and second pairs of articulations. The rigid support members 78 and 79, and the support members 83a, 83b and 87a, 87b (support members are referred sometimes here with reference sign "83" and "87") are generally more rigid than the articulations 80a-80b and 81a-81d. Accordingly, the support member 78, the first support member 83a, and the second support member 83b of the first actuation member may be referred to collectively as rigid support members. Likewise, the support member 79, the first support member 87a, and the second support member 87b of the second actuation member 76 may also be referred to collectively as rigid support members.

Referring to FIG. 4A, the thickness of the first and second actuation members 74 and 76 can vary along the respective actuation member axes 4 and 5. For instance, the support members 78, 83, and 79, 87 can have each have thickness that is different compared to the thickness of each articulations 80a-80d and 81a-81d. This difference in thickness can facilitate deforming the actuator 82 into the actuated configuration. The first and second actuation members 74 and 76 define a support member thickness T1 and T2 at the respective support members 78, 83a, 83b and 79, 87a, 87b. The support member thickness T1 extends from the inner surface 88a to the outer surface 88b along a direction that is perpendicular to the respective first actuation member axis 4. The second actuation member support member thickness T2 extends from the inner surface 90a to the outer surface 90b along a direction that is perpendicular to the second actuation member axes 5. Thickness T1 can vary among each support member 78, 83a, and 83b. Further, thickness T2 can vary for each support member 79, 87a, and 87b.

Continuing with FIG. 4A, each articulation defines a thickness that is generally less than the support member thicknesses. For instance, each articulation along the first actuation member 74 defines a first articulation thickness D1 (not shown) that is perpendicular the first actuation member axis 4. The articulation thickness D1 is less than the thickness of the support member 78, the first support member 83a, and the second support member 83b. Each articulation 81 along the second actuation member 76 defines a second articulation thickness D2 that is perpendicular to the second actuation member axis 5. The second articulation thickness D2 is less than the thickness of the support member 79, the first support member 87a, and the second support member 87b. It should be appreciated that the articulation thickness D1, D2 may vary for each articulation along the first and second actuation members 74 and 76.

Referring now to FIGS. 4C and 4D, the articulations 80a-80d and 81a-81d can define stress risers along the respective actuation members 74 and 76 formed by the transition between the support member thicknesses T1, T2 and the articulation thicknesses D1, D2. Forces F1 and F2 applied to the actuator 82 causes localized bending at the stress risers, which in turns causes the rigid support members 78, 83a, 83b, 79, 87a, 87b to bend relative to the first and second sets of articulations 80a-80d, and 81a-81d, respectively. Accordingly, compressive forces F1 and F2 applied to the first and second actuation members 74 and 76 cause pronounced bending at the articulations 80a-80d and 81a-81b, while other portions of the actuation members 74 and 76, such as the rigid support members, are subject to less bending. Thus, the actuator 82 is adapted to have flexibility that permits the first and second actuation members 74 and 76 to bend in response to loads applied by a user's hand and a stiffness that causes retainer 86 to displace relative to the bearing member 84. Further, the actuator 82 has a resiliency that causes the first and second actuation members 74 and 76 to revert their respective undeformed positions when forces F1 and F2 are released from the actuator 82.

The actuator 82 is configured to have a first shape in the initial configuration (FIGS. 1A and 4C) and a second shape that is different than the first shape when the actuator 82 is in the second actuated configuration (FIGS. 1B and 4D). In accordance with the illustrated embodiment, each actuation member 74 and 76 can define a generally trapezoidal shape with respect to the retainer 86 when the actuator is in the initial configuration. In addition, the actuation member 74 and 76 can define a generally linear shape that is aligned with the longitudinal direction L when the actuator 82 is in the actuated configuration (FIGS. 1B, 4D). Application of the compressive forces F1 and F2 to the flexible portion 89 of the actuator 82 cause the first and second actuation members 74 and 76 to bend at each articulation 80a-80d, 81a-81d, while bending in the rigid support members 78,83, 79,87 is minimized. This results in the first and second actuation members 74 and 76 flexing into the generally linear shape as illustrated in FIGS. 1B and 4D. When compressive forces F1 and F2 are removed from the instrument 22, the first and second actuation members 74 and 76 revert or spring back into the initial configuration with the generally trapezoidal shape as shown in FIGS. 1A and 4C. Accordingly, it can be said that the shape of the actuator 82 is configured such that application of a forces sufficient to deform the actuator 82 will overcome frictional forces acting between 1) the bone fixation member 24 and the locking mechanism 38, and 2) the bone fixation member 24 and the bone, thereby causing displacement of the retainer 86 and the attached the bone fixation member 24 relative the locking mechanism 38. For instance, if a user applies opposing forces F1 and F2 to the actuator 82 along a direction that is perpendicular to the longitudinal direction L, the first and second actuation members 74 and 76 deform, causing the select location 85 to move away from the bearing member 84, which causes the retainer 86 to retract the bone fixation member 24 away from the locking mechanism 38. When forces F1 and F2 are applied the actuator 82 to deform the actuator 82, the deformed actuator 82 stores a potential energy that is sufficient to return the actuator 82 to its initial configuration. When the forces F1 and F2 are released, the potential energy stored in the deformed actuator 82 causes the actuator 82 to revert to its initial configuration.

The first and second actuation members 74 and 76 can have or include any other structure, device, or feature, or have any shape, that is adapted to allow deformation of the actuator 82 and resultant movement of the retainer 86 along the longitudinal direction L. In accordance with an alternative embodiment, each articulation can be configured as a groove defined at one or both of the inner surfaces 88a, 90a and the outer surfaces 88b, 90b. Such a groove may extend partially or completely across the actuator axes 4, 5. In other alternative embodiments, the articulations can be configured as a hinge. The articulations can include any other structure, or device, or feature that will permit a rigid support member to pivot relative to the adjacent pivot support member. Further, the first and second actuation members 74 and 76 can be configured without articulations described above. In accordance with such an alternative embodiment, the first and second actuation members 74 and 76 can be curved with respect to a point (not shown) defined by the retainer 86. For instance, the first and second actuation members can be elongate along respective curved axes. Each curved axis can have one radius of curvature, or alternatively multiple radii of curvature. For instance, the curved actuation members can have a curved axis in the shape of a semi-circle. Further, the curved actuation members can have any number of cross-sectional shapes, such as circular, rectilinear, square and the like.

Referring to FIGS. 4C and 4D, applying forces F1 and F2 to the flexible portion 89 of the actuator 82 causes the actuation members 74 and 76 to deform, thereby causing proximal end 68 of the instrument 22 to move along the longitudinal direction L away from the bearing member 84. The result is increasing the distance X between the select location 85 and the bearing member 84 when the actuator 82 is actuated. In accordance with the illustrated embodiment, the select location 85 is spaced a distance X from bearing member 84 in the longitudinal direction L when the actuator 82 is in the first configuration. When the actuator 82 is actuated into the second configuration, the actuation members 75 and 76 deform causing the select location 85 to move further away from the bearing member 84 thereby increasing the distance. For instance, instrument 22 can have a first distance X that extends from the location 85 of the actuator 82 to the bearing element 84 when the actuator 82 is in the first configuration. The instrument 22 defines a second distance Y that extends from the location 85 of the actuator 82 to the bearing element 84 that is greater than the first distance X when the actuator 82 is in the second actuated configuration. Further, it can be said that when the actuator 82 is in the first or initial configuration as shown in FIG. 4C, the instrument 22 has a first effective length 2 that extends from the distal end 66 to the proximal end 68 along a longitudinal axis 8 that is aligned with the longitudinal direction L. When the actuator 82 is in the actuated configuration as shown in FIG. 4D, the instrument 22 has a second effective length 3 that extends from the distal end 66 to the proximal end 68 along the longitudinal axis 8 that is greater than the first effective length 2. The difference between the second effective length 3 and the first effective length 2 corresponds to the extent that the retainer 86 is moved relative to the bearing member 84. In the illustrated embodiment, when the instrument 22 has not been actuated, the distal end 16 of the retainer 86 is spaced from the inner surface of the distal wall 94 a distance E1. When the instrument 22 is actuated, the distal end 16 of the retainer 86 is spaced from the inner surface of the distal wall 94 a distance E2. The difference between distance E2 and E1 is the extent of retainer 86 displacement relative to the bearing member 84. While the illustrated embodiment shows the distal end 16 of the retainer 86 spaced from the distal wall 94 a distance E1, the retainer 86 can abut the distal wall 94 in an initial configuration. In such an embodiment, E1 may be at or near zero (0).

Referring now to FIGS. 5A-5C, the instrument 22 may include at least one cutting assembly 120 configured to cut the implant 24 when the retainer 86 is attached to the implant 24. The cutting assembly 120 may include one or more blades supported by the bearing member 84 and configured to cut the implant 24. The bearing member 84 is configured to carry at least one blade 101, such as a pair of blades 101 and 102. The first blade 101 extends from the first wall 92 toward the channel 95 and the second blade 102 extends from the second wall 93 toward the channel 95 and is spaced from the first blade 101. The first and second blades 101 and 102 are positioned on the retainer 86 to define a gap 106 that extends between the blades 101 and 102. The gap 106 has a gap dimension that extends along the lateral direction A. The channel 95 can have a channel dimension that extends along the lateral direction A that corresponds to the gap dimension. In other embodiments, the gap dimension can be slightly less than the channel dimension or greater than the channel dimension. The bearing member 84 can include a coupler 108 that retain the blades 101 and 102 in position on the bearing member 84. In the embodiment illustrated in FIGS. 5A-5C, the coupler 108 includes grooves 110a and 110b sized to receive the respective blades 101 and 102, and at least one projection 112 spaced from the grooves 110a and 110b toward the channel 95. One end of the blades 101 and 102 are held in the grooves 110a and 110b and the opposed ends of the blades 101 and 102 are biased against the projection 112. The strap 32 has a width W that extends in the transverse direction T such that the strap width W is less than the gap dimension. Because the strap width is less than the gap dimension, rotation of instrument 22 along a rotational direction 13 about the axis 8 causes the blades 101 and 102 to cut into the received strap 32 while torsional force applied to the strap 32 shears the strap 32.

Figure 6A:
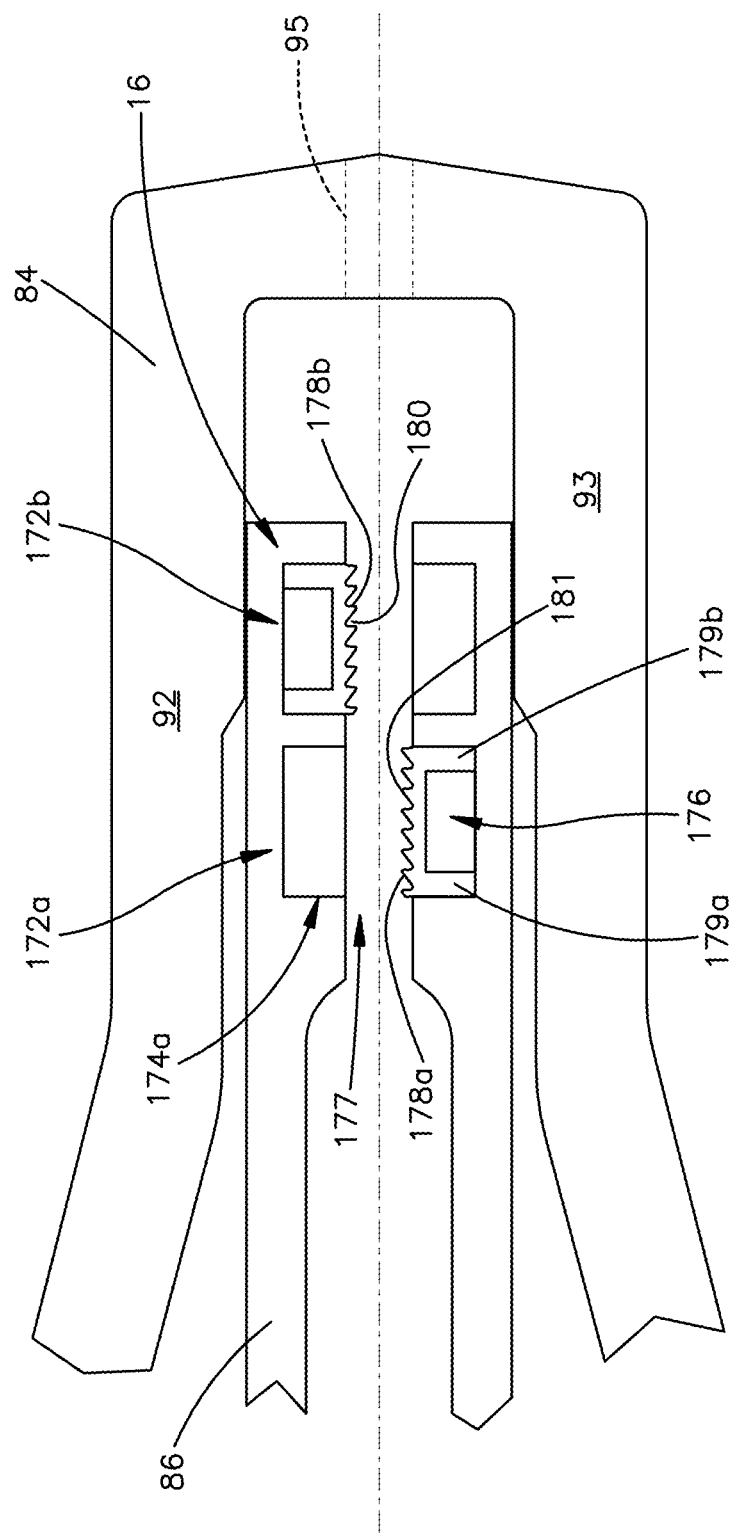

Referring to FIGS. 6A-6B, the instrument 22 may include one or more locking assemblies configured to secure a portion of the implant 24 to the retainer 86. As illustrated, the distal end 16 of the retainer 86 supports a first locking assembly 172a and a second locking assembly 172b. The locking assemblies 172a and 172b are substantially similar. Accordingly, only the first locking assembly 172a will be described below. In accordance with the illustrated embodiment, the locking assembly 172a includes a locking member 174a configured to secure the strap 32 to the retainer 86. When the strap 32 is secured to the retainer 86, movement of the retainer 86 along the longitudinal direction L can apply tension along the strap 32. The locking member 174a includes a lock body 176, a slot 177 that extends through the lock body 176, and at least one complementary tooth such as a plurality of locking teeth 178a that extend into the slot 177. The lock body 176 includes legs 179a and 179b coupled to the retainer 86. Further, the lock body 176 defines a first surface 180 and an opposed second surface 181. The second surface 181 can define the teeth 178a. The first and second surfaces 180 and 181 can at least partially define the slot 177. In an alternate embodiment, the legs 179a and 179b can be flexible so as to permit iteration of the locking member 174a to transition or bias between one or more positions.

The retainer 86 can support the first locking assembly 172a in a first orientation and support the second locking assembly 172b in a second orientation that is opposite the first orientation. Thus, the instrument 22 can be attached to the strap 32 of the implant 24 regardless of how the instrument 22 is orientated relative to the strap 32. For instance, the first locking assembly 172a is disposed in the retainer 86 such that the teeth 178a extend generally toward the wall 92. The second locking assembly 172b is disposed in the retainer 86 such the teeth 178b are disposed generally toward the wall 93. In this regard, the first orientation can be when the teeth 178a (or 178b) extend toward wall 92 and the second orientation is opposite the first orientation such that the teeth 178a (or 178b) extend toward the wall 93.

In accordance with an alternative embodiment, the instrument 22 can be configured to selectively advance the implant 24 along the proximal direction 7. For instance, the retainer 86 channel 95 configured to receive a portion of an implant 24. The retainer 86 includes an inner surface, for instance the surfaces of locking assemblies 172a and 172b, that is configured to selectively engage and disengage the received portion of the implant 24. The actuator 82 can be operable to move the retainer 86 relative to the bearing member 84 from a first position to a second position displaced from the first position along a proximal direction, and to subsequently return the retainer 86 from the second position to the first position long the distal direction that is opposite the first direction. The retainer 86 is configured to engage the received portion of the implant 24 as the retainer 86 moves in the proximal direction, and disengage from the received portion of the implant 24 as the retainer moves in the distal direction. Engagement and disengagement between retainer and the portion of the implant can be repeated to advance the implant 24 further through the channel 95 of the retainer.

Turning to FIGS. 7A and 7B, the instrument 422 can be configured similarly to the instrument 22 described above. The instrument 422 can include an actuator 482, a bearing member 484, and a retainer 486. The description for instrument 422 below will use the same reference numbers for elements that are common to both instruments 22 and 422. The bearing member 484 and retainer 486 in instrument 422 are similar to the bearing member 84 and retainer 86 of instrument 422. Thus, the bearing member 484 can define a receptacle that is similar to the receptacle 67 above. The receptacle is sized to receive a distal end 416 of the retainer 486 and define a friction fit with between walls 93 and 94 and retainer distal end 416. In addition, the bearing member 484 carries a cutting assembly 120. Further, the instrument 442 can include a locking assembly 442 that is similar to the locking assembly 172 described above and illustrated in FIGS. 6A-6B. For instance, the locking assembly 442 is configured similarly to the locking assemblies 172a and 172b discussed above. As such, the locking assembly 442 may include locking member 174, which includes the lock body 176, a slot 177 that extends through the lock body 176, and locking teeth 178 that extend into the slot 177.

Continuing with FIGS. 7A and 7B, the actuator 482 can be a curved body 464 configured to actuate the retainer 486 from a first position as shown in FIG. 7A into a second position (not shown) in the proximal direction 7. The curved body 464 or actuator 482 can include a first curved actuation member 474 and a second actuation member 476. The first or curved actuation member 474 is elongate along a curved axis 404 between the instrument proximal end 68 and the bearing member 484. The first actuation member 474 includes side extensions 478a and 468b that extend outwardly with respect to the axis 404 to define a hand support. The second actuation member 476 is elongate along a curved axis 505. The second actuation member 476 includes grip holes 450a, 450b, and 450c. The grip holes 450a, 450b, and 450c are sized to receive a user's fingers. A user can grip the actuator 482 such that the user's palm is adjacent to the extensions 478a and 478b and the user's fingers can extend into holes 450a-450c. The curved actuator 482 is configured such that when the instrument 422 is in the first or initial configuration, forces are sufficient to deform the flexible portion are sufficient to overcome the frictional forces acting between the bone fixation member 24 and the locking mechanism 38 so that the bone fixation member 24 is advanced a sufficient distance for reduction of the osteotomy location 30. Application of the force F1 and F2 to the curved actuator 482 along a direction that is perpendicular to the longitudinal direction L causes the first and second curved actuation members 474 and 476 to deform into a more linear shape, which causes the retainer 486 to retract in the proximal direction 7 when the implant 24 is attached to the retainer 486. When the forces F1 and F2 are applied to deform the instrument 422, thereby deforming the actuator 482, the deformed actuator 482 stores a potential energy that is sufficient to return the actuator 482 back to the initial configuration. When the forces F1 and F2 are removed from the instrument 422, the actuator 482 reverts back to its initial configuration.

Figure 8A:
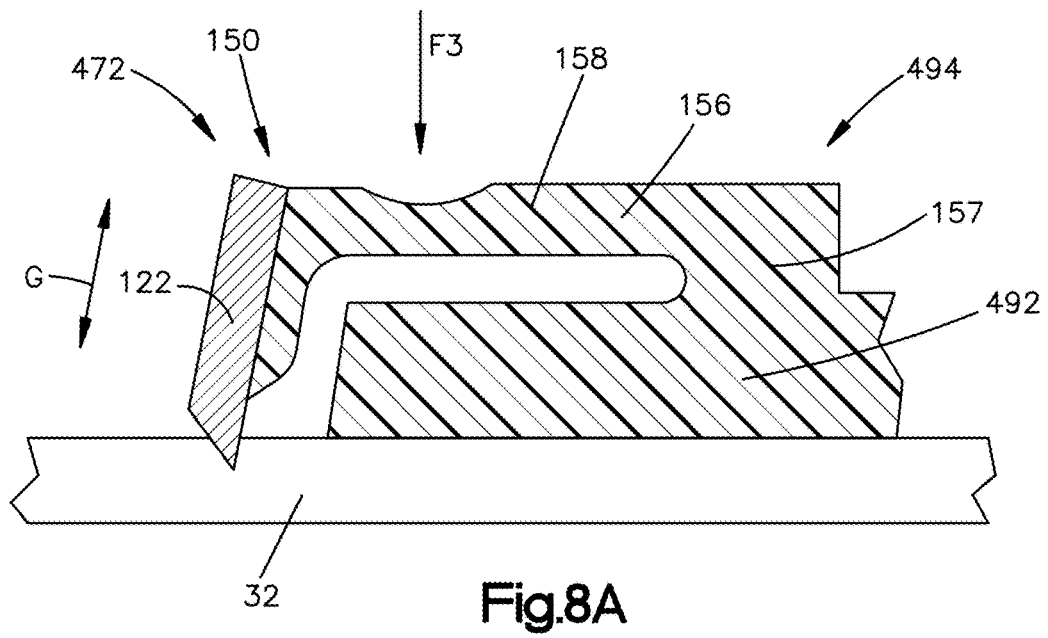
FIG. 8A is a sectional view of a portion an instrument according to another embodiment of the present disclosure.
Figure 8B:
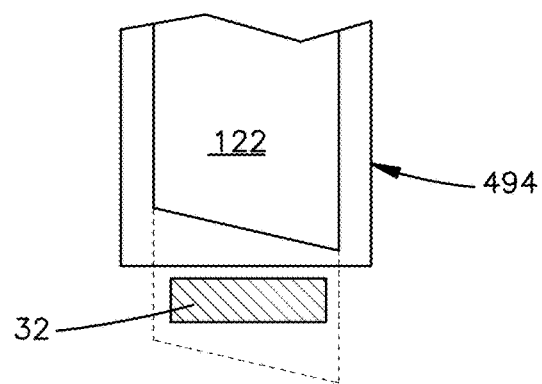
FIG. 8B is an end view of the instrument shown in FIG. 8A, showing a cross-section of the bone fixation member.

Turning to FIGS. 8A and 8B, an instrument 472 in accordance with another embodiment of the present disclosure is illustrated. The instrument 472 is constructed substantially similar to the instrument 22 described above and shown in FIGS. 1A-6C. Elements common between instruments 22 and 472 have the same reference numbers unless noted otherwise. In accordance with the alternate embodiment, the instrument 472 includes a bearing member 494 that extends from the actuator 82 (not shown). The bearing member 494 can include an upper wall 492 and a cutting assembly 150 that is supported by the upper wall 492 and is configured to cut the implant 24. The cutting assembly 150 includes at least one blade 122 supported by an actuator 156. The actuator 156 is configured to move blade 122 along a direction G that is aligned with or offset with respect to the lateral direction A. Movement of blade along the direction G cuts the implant 24 by severing the retained portion of the strap 32 from the locking mechanism 38 (not shown). The actuator 156 can be a lever 158 connected to the bearing member 494. The bearing member 494 and lever 158 can be monolithic or separate pieces. The lever 158 includes a base 157 that is connected the wall 92 of the bearing member 494, and a support member 159 that receives and is attached to the blade 122 and extends toward the strap 32. The lever 158 is configured to bias the blade 122 away from the strap 32 along the lateral direction A. Application of a force F3 to the lever 158 biases the lever 158 toward the bearing member 494, which in turn causes the blade 122 to cut the strap 32. In other embodiments, the cutting assembly 150 can include an additional actuator positioned on a wall (not shown in FIGS. 8A and 8B) opposite wall 492 of the bearing member 484.

Figure 9A:
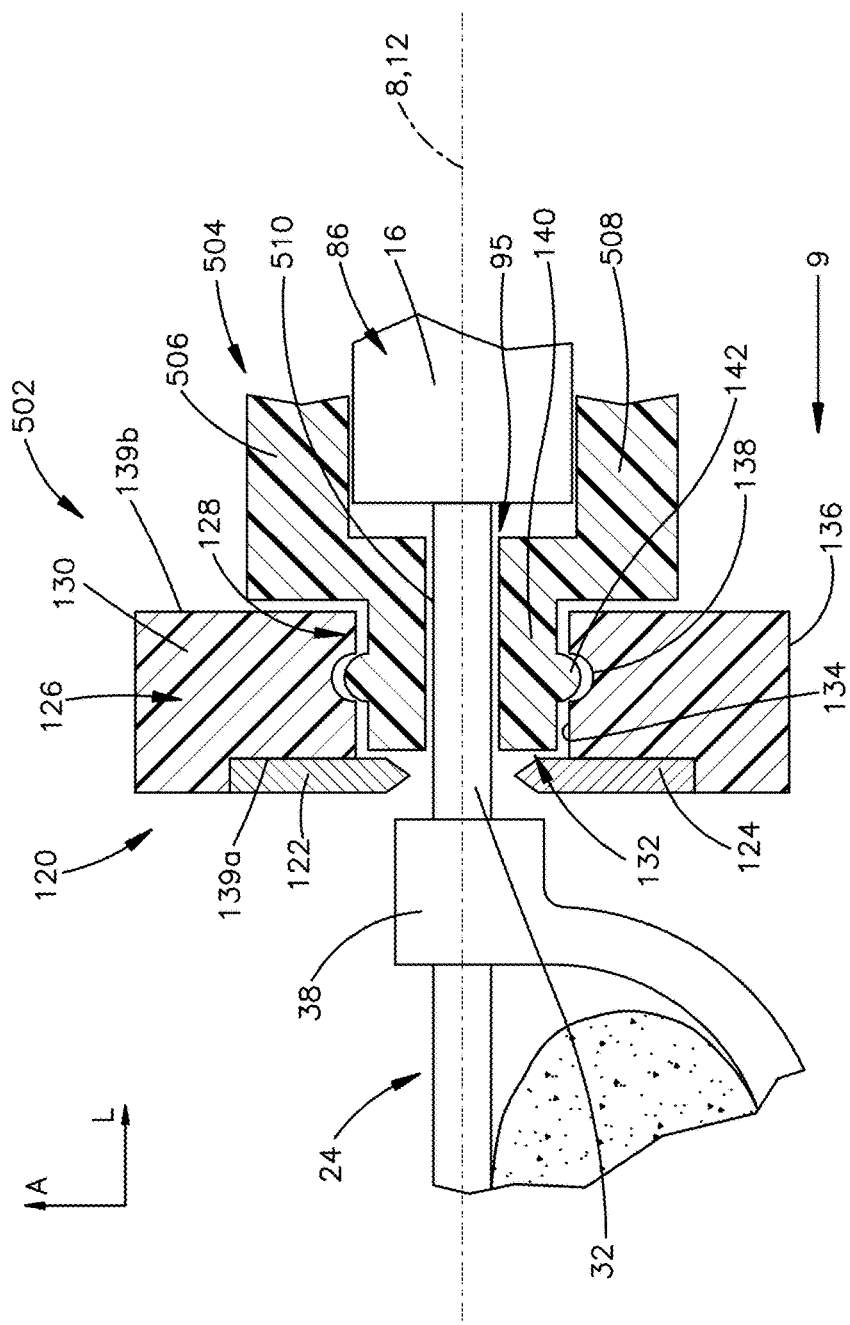
FIG. 9A is a sectional view of a portion of an instrument according to another embodiment of the present disclosure, showing the instrument holding a bone fixation member around an underlying bone.
Figure 9B:
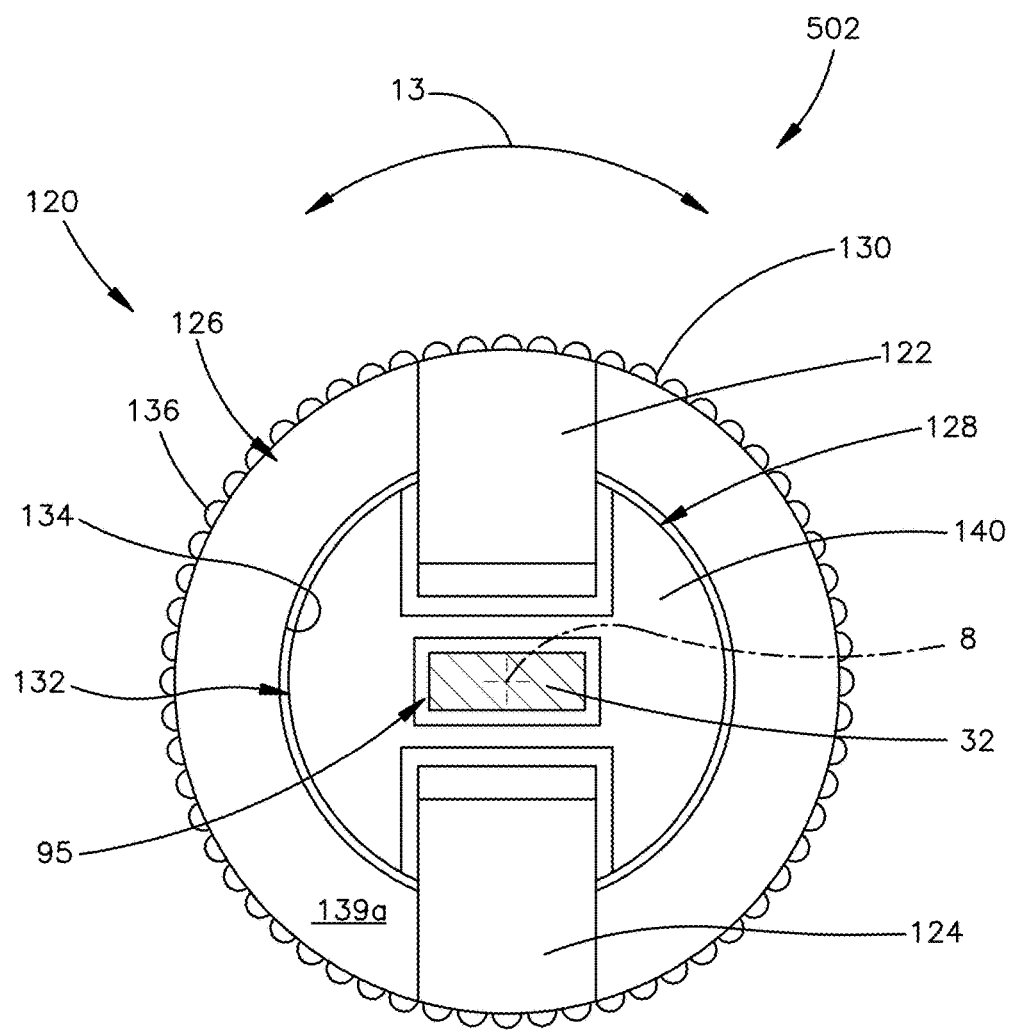
FIG. 9B is an end view of the instrument shown in FIG. 9A, showing a portion of the bone fixation member and the underlying bone removed.

Turning to FIGS. 9A and 9B, another instrument 502 includes a bearing member 504 and a cutting assembly 120 configured to cut the implant 24, according to another embodiment of the disclosure. The instrument 502 is similar to the instrument 22 and similar reference signs are for elements common to instruments 22 and 502. In accordance with the illustrated embodiment, the bearing member 504 includes a first or upper wall 506, a second or lower wall 508, and a third or distal wall 510. The bearing member 504 also includes coupling member 128 that projects from the distal wall 510 along the axis 8. The instrument 502 also includes a cutting assembly 120 that includes at least one, such as pair of blades 122 and 124 supported by a blade actuator 126. The blade actuator 126 is rotatably coupled to the coupler member 128, such that blade actuator is rotatable with respect to the bearing member 504. The blade actuator 126 positions the blades 122 and 124 relative to the strap 32. The blade actuator 126 is configured to rotate relative to the bearing member 504 of the instrument 22. The blade actuator 126 includes a body 130 that extends along the axis 8.

The body 130 defines a bore 132 that extends along the axis 8. The body 130 further defines an inner surface 134 and an opposed outer surface 136 spaced from inner surface 134 along a direction that is perpendicular to axis 8. The inner surface 134 defines the bore 132. The inner surface 134 also defines an engagement member 138, such as a recess. The body 130 also defines a distal facing surface 139 that is configured to carry the blades 122 and 124. In accordance with one embodiment, the distal facing surface 139 defines a pair of cutouts (not numbered) that receive and hold the blades 122 and 124 on the actuator 126. The coupler 128 may include a projection 140 that extends from the bearing member 504 along the distal direction 9 into the bore 132, and an engagement member 142 coupled to the blade actuator 126. The projection 140 is sized to fit within the bore 132 so that the blade actuator 126 can rotate relative to the projection 140 about the axis 8 in the rotational direction 13. The engagement member 142 fits within the complementary shaped engagement member 138 on the blade actuator 126. The engagement members 138 and 142 are configured to retain the blade actuator 126 in position on projection 140 along a longitudinal direction, yet permit the blade actuator 126 to rotate about the projection 130 in the rotational direction 13. Accordingly, the engagement member 138 can be annular groove defined by the body 130 and the engagement member 142 can be ridge that extends around the perimeter of the projection 140. It should be appreciated the engagement member 138 can be a ridge and the engagement member 142 can be a groove or recess. The blades 122 and 124 are spaced apart to define a blade gap distance B1 that extends in the lateral direction A between the blades 122 and 124. The strap 32 has a width W that extends in the transverse direction T such that the strap width W is less than the blade gap distance B. As blade actuator 126 is rotated along a rotational direction 13, the blades 122 and 124 cut into the strap severing the retained portion of the strap 32 from the locking mechanism 38.

Turning to FIGS. 10A-10F, one or more blade configurations may be used with any of the cutting assemblies described above. In accordance with the illustrated embodiment, the blade 100 can include a blade body 103 and pair of cutting edges 104a and 104b angularly offset with respect to an axis 109. The cutting edges 104a and 104b intersect to define a blade tip 105. Further, the blade body 103 may have a cross-sectional shape that is V-shaped. In other embodiment shown in FIGS. 10C and 10D, the cutting edge 104 is curved. Further, the blade body 103 may have a cross-sectional shape that is U-shaped. In addition, the blade 100 can have cutting edge 104 that is angulate offset with respect to the blade axis 109. The blade body 103 may have a cross-sectional shape that generally linear. While several blade configurations are illustrated, it should be appreciated that any blade configuration can be used with the instrument 22.

Turning now to FIG. 11, an instrument 522 according to another embodiment of the present disclosure include a bearing element 526 and a stabilizing assembly 160 configured to couple the instrument 522 to the locking mechanism 38, yet permit the instrument 552 to rotate relative to the stabilizing assembly 160 and locking mechanism 38 so as to cut the retained portion of the strap 32. The instrument 522 is constructed substantially similar to the instrument 22 described above and shown in FIGS. 1A-6B. Accordingly, elements common to instruments 22 and 522 will use similar reference numbers. In accordance with the alternative embodiment, the bearing member includes opposed walls 524 and 525, and a distal wall 527. The stabilizing assembly 160 includes a body 162 that defines a front end 164, a rear end 161 spaced from the front end 164 along the longitudinal direction L, and a bore 166 extending therethrough along the longitudinal direction L. The body 162 further defines an inner surface 168 that extends between the front and rear ends 164 and 161. The inner surface 168 defines the bore 166. The bore 166 includes a front, or implant receptacle portion 170a and a rear, or instrument receptacle portion 170b. The implant receptacle portion 170a is sized and configured to mate with an outer surface of the locking mechanism 38 of the implant 24. The rear portion 170b is sized and configured to receive the bearing member 84. The body 162 includes legs 163a and 163b that partially define the rear portion 170b of the bore 166. The legs 163a and 163b include respective first engagement members 165a and 165b. The walls 524 and 525 define second engagement members 167a and 167b shaped to mate with the first engagement members 165a and 165b. In accordance with the illustrated embodiment, the first engagement members 165a and 165b are projections and the second engagement member 167a and 167b are complementary shaped recesses or grooves. It should be appreciated the engagement members 165a and 165b may be a recess and the engagement members 167a and 167b may be grooves. When the stabilizing assembly 160 is coupled to the locking mechanism 38 and the bearing member 84 of the instrument is received in the bone portion 170b, the instrument 522 is rotatable about the axis 8, relative to the stabilizing assembly 160 and the locking mechanism 38. In an alternative embodiment of instrument 522, the engagement member 165a and 165b could extend circumferentially about the axis 8. In such an embodiment, the distal end 66 of the instrument 522, for instance the bearing member 526, may have a circular cross-sectional shape that conforms to a similarly shape portion of the bore 166. Further, the engagement members 167a and 176b could extend circumferentially around the bearing member 526 to engage with the circumferentially disposed engagement members 165a and 165b.

In an alternate embodiment, the instrument 522 may be selectively decoupled from the stabilizing assembly 160 so that the instrument 522 can rotate relative to the stabilizing assembly 160 and the locking mechanism 38. In such an embodiment, the legs 163a and 163b are spaced apart and define a gap that extends therebetween. The bearing member 84 is coupled to the stabilizing assembly 160 as described above. In accordance with the alternative embodiment, in order to rotate the instrument 522, the bearing member 84 can be decoupled from the stabilizing assembly 160 by biasing the bearing member 84 out of engagement with the legs 163a, 163b. For instance, the legs 163a, 163b can flex outwardly as the bearing member 84 is pulled in proximal direction 7 so the engagement members 165 and 167 disengage. When the bearing member 84 is decoupled, the instrument 522 may be rotated as needed to cut the strap 32.

As shown in FIGS. 12A and 12B, another embodiment of an instrument 562 includes a locking assembly 572 carried by a retainer 586. The instrument 562 is similar to the instrument 22 described above and therefore the description of instrument 562 below will use the same reference numbers for elements that are common between instruments 22 and instrument 562, such as the actuator 82, bearing member 84, and the cutting assembly 120. In accordance with the alternative embodiment, the retainer 586 carries the locking assembly 572 and the locking assembly 572 is configured to transition between a locked configuration as shown in FIG. 12A wherein the inserted strap 32 is fixed to the retainer 586, and an unlocked configuration as shown in FIG. 12B, wherein the locking assembly 572 is not secured to the strap 32 such that the strap 32 is permitted to translate along the retainer 586 in the distal direction 9.

Continuing with FIGS. 12A and 12B, in accordance with the illustrated embodiment, the locking assembly 572 includes a locking member 574. The locking member 574 includes a lock body 576 and at least one tooth such as a plurality of locking teeth 578. The lock body 576 includes legs 579a and 579b coupled to the retainer 586. The legs 579a and 579b are flexible so as permit transition of the locking member 574 between the locked and unlocked configurations. Further, locking assembly 572 can include a surface 581 opposed to the teeth 578. The surface 581 does not have teeth. The distal end 516 of the retainer 586 defines at least one chamber 19 sized to hold the locking member 574. The retainer 586 can define a retainer inner surface that includes opposed surface portions 17a and 17b. The retainer inner surface can at least partially define the chamber 19. The retainer inner surfaces 17a and 17b may be referred to as an inner surface 17. The legs 579a and 579b are spaced apart from the respective surface portions 17a and 17b so as to provide clearance for the lock body 576 to move between the locking and unlocked configurations. When the strap 32 is inserted into the retainer 586 through the channel 95, the strap 32 translates along the proximal direction 7 over the locking member 174 so that strap teeth 48 engage locking member teeth 578. Further translation of the strap 32 causes the legs 579a and 579b to flex, biasing the locking member 574 into the unlocked configuration (FIG. 12B) such that the strap 32 can further translate in the proximal direction 7. When the instrument 522 is actuated such that the retainer 586 is displaced, and is therefore retracted away from the locking mechanism 38 of the bone fixation member 24 in the proximal direction 7, the locking member 574 is biased into the locked configuration (FIG. 12A) wherein the teeth 48,578 engage to prevent the strap 32 from translating in the distal direction 9.

Figure 13:
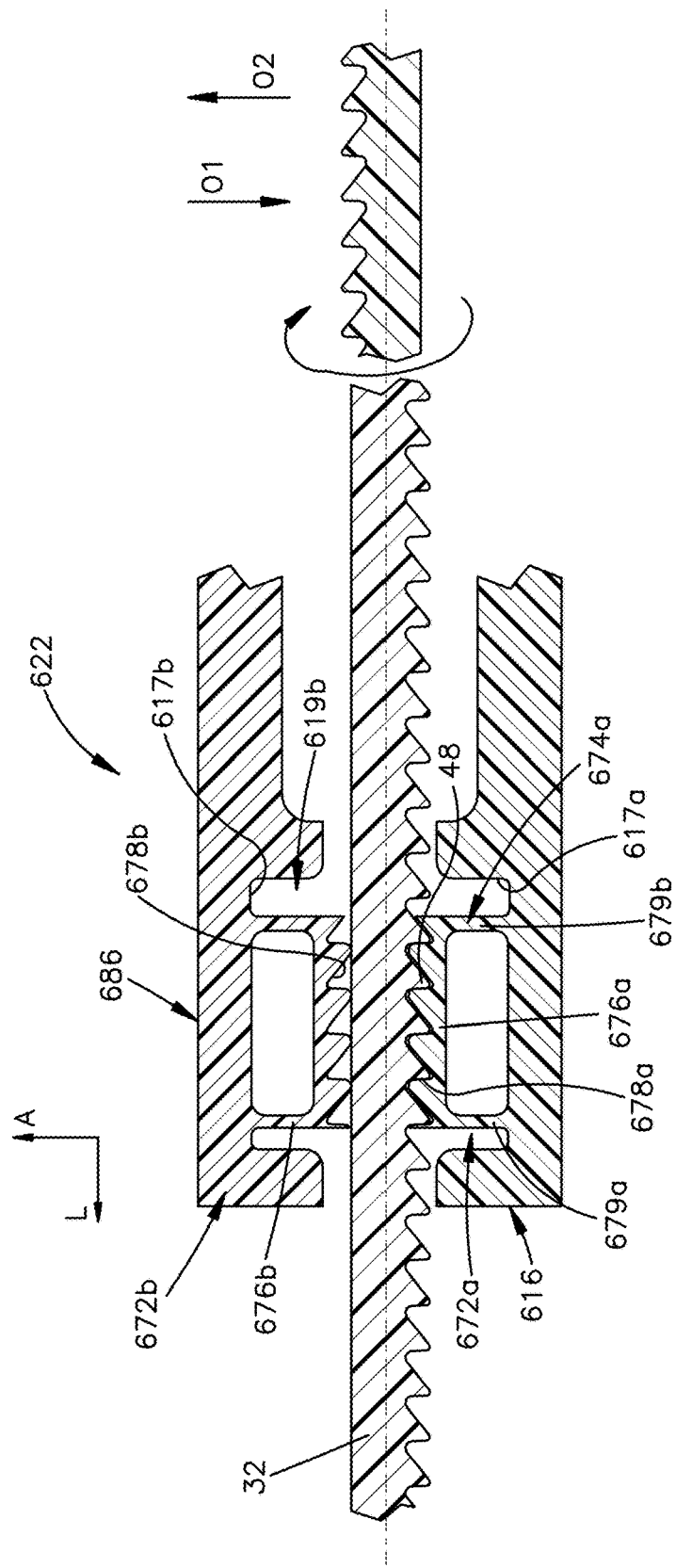
FIG. 13 is a sectional view of a portion of an instrument according to another embodiment of the present disclosure.

In the embodiment illustrated in FIG. 13, an instrument 622 according to another embodiment of the present disclosure includes a bearing member 84, a retainer 686, and locking assemblies 672a and 672b carried by the retainer 686. The instrument 622 is similar to the instrument 22 and 562 described above. The locking assembly 672a is substantially similar the locking assembly 672b, thus only locking assembly 624a will be discussed below. The locking assembly 672a includes a locking member 674a. The locking member 674a includes a lock body 676a and at least one complementary tooth such as a plurality of locking teeth 678a. The lock body 676a includes legs 679a and 679b coupled to the retainer 686. In use, the first locking assembly 672a is disposed in the retainer 686 such that the teeth 678a extend generally toward teeth 678b of the second locking assembly 672b. In this regard, the first locking assembly 672a can be supported by the retainer 686 in a first orientation and the second locking assembly 672b is supported by the retainer 686 in a second orientation that is opposite the first orientation, similar to the locking assemblies 172a and 172b described above. During use, the instrument 622 can attach to the strap 32 of the implant 24 regardless of how the instrument 622 is orientated relative to the strap 32. The distal end 616 of the retainer 686 defines at least one chamber, such as a pair of chambers 619a and 619b sized to house the locking assemblies 672a and 672b. The retainer 686 can define a retainer inner surface s 617a and 617b that at least partially defines respective chambers 619a and 619b.

Turning to FIG. 14, an instrument 722 according to another embodiment of disclosure includes a first and second locking assemblies carried by a retainer 786. The instrument 722 is similar to the instrument 22 described above and therefore the description of instrument 722 below will use the same reference numbers for elements that are common between instruments 22 and instrument 722, such as the actuator 82, bearing member 84, and the cutting assembly 120.

Continuing with to FIG. 14, the instrument 722 can include the locking assemblies that may be configured as first and second locking inserts 182 and 183. The inserts 182 and 183 are configured similarly and thus only one insert 183 will be described below. The insert 183 includes a lock body 776, teeth 778, and flexible legs 779a and 779b. The legs 779a and 779b are coupled to the retainer 786. The retainer 786 can include an upper chamber 719a and an opposed lower chamber 719b that hold the first and second locking inserts 182 and 183, respectively. The retainer 786 can include an upper wall 31a that is angularly offset with respect to lateral direction A so as define an upper beveled surface 184a, and a lower wall 31b that is angularly offset with respect to the lateral direction A to define a lower beveled surface 184b. In accordance with the illustrated embodiment, the inserts 182 and 183 are configured to transition between a locked configuration and an unlocked configuration. For instance, the legs 779a and 779b are flexible in order to allow the insert 183 to bias between an unlocked configuration (not shown), wherein the strap 32 is moveable along the retainer 786, and the locking configuration, wherein the strap teeth 48 are engaged with the teeth 778 of the insert 182 and the strap 32 is attached to the retainer 786. The beveled surfaces 184a and 184b provide room for the inserts 182 and 183 to bias from locked configuration into the unlocked configuration. Further, use of the two inserts 182 and 183 permit the strap teeth 48 to engage with the teeth 778 and 781 of the locking inserts 182 and 183 regardless of how the instrument 722 is orientated with respect to the strap 32, as described above with respect instrument 22.

Turning to FIG. 15, an instrument 822 according to another embodiment of the present disclosure includes a locking assembly, configured as a locking insert 186, carried by a retainer 886. The instrument 822 is similar to the instruments 22 and 722 described above. The description of instrument 822 below will use the same reference numbers for elements that are common between instruments 22, 722, and 822. The locking insert 186 is configured to iterate between a locked configuration and an unlocked configuration. As illustrated, the insert 186 includes the lock body 876 that a pair of legs 879 and 881. The legs 879 and 881 terminate at engagement members 883 and 885, respectively. The retainer 886 includes a surface 817 that least partially defines the chamber 819, walls 821a and 821b, and a beveled portion 884. In accordance with the alternative embodiment, the inner retainer surface 817 can define a pair of complementary shaped engagement members 893 and 895 that receive the engagement members 883 and 885, respectively, thereby coupling the locking assembly 874 to the retainer 886. As noted above, the legs 879 and 881 may be flexible to permit the insert 186 to bias between the locked configuration and an unlocked configuration as described above.

Figure 16A:
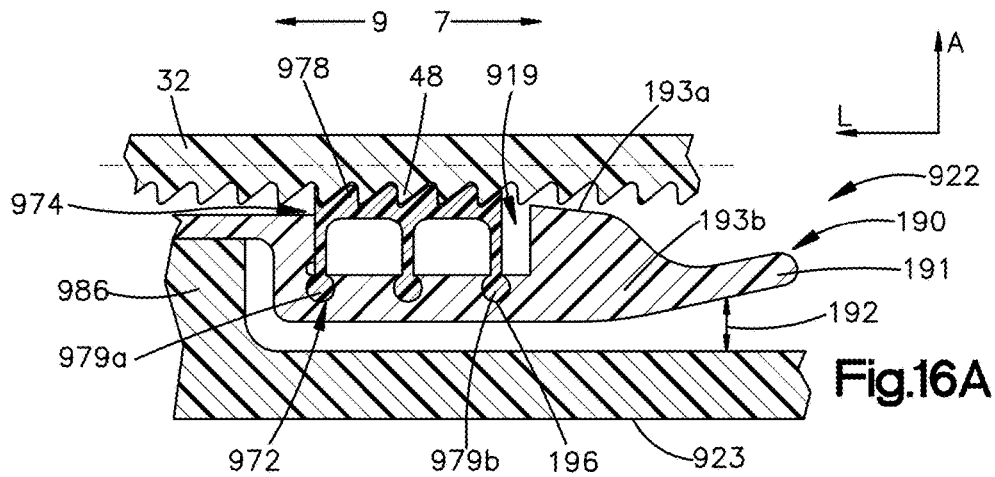
FIG. 16A is a sectional view of a portion of an instrument according to another embodiment of the present disclosure.
Figure 16B:
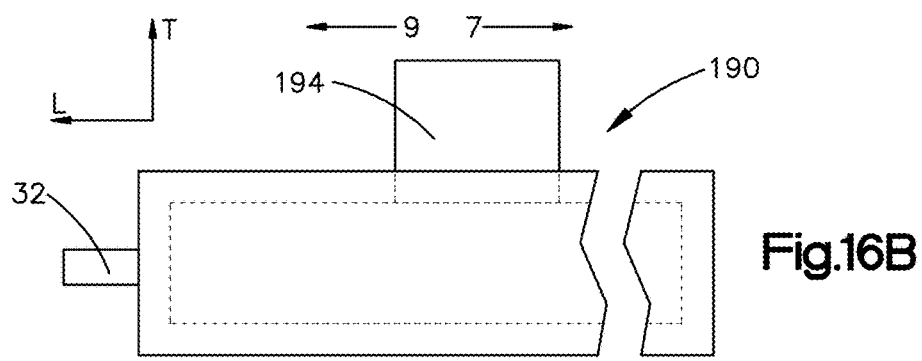
FIG. 16B is a schematic top view of a portion of the instrument shown in FIG. 16A.

Referring now to FIGS. 16A and 16B, an instrument 922 according to another embodiment of the disclosure is configured to permit the selective release the attached portion of the implant 24 from the retainer 986. The instrument 922 is similar to the instrument 22 described above and therefore the description of instrument 922 below will use the same reference numbers for elements that are common between instruments 22 and instrument 992, such as the actuator 82 and bearing member 84, and cutting assembly 120. In accordance with the illustrated embodiment, the retainer 986 can include one or more release actuators 190 that selectively 1) couple the locking assembly 972, and thus the retainer 986, to the received portion of the implant 24, and 2) decouple the locking assembly 972 from the received portion of the implant 24. The locking assembly 972 includes a locking member 974. The locking member 974 includes legs 979a and 979b and teeth 978. As shown in FIGS. 16A and 16B the actuator 190 is configured as a lever 191 that is biased upwardly away from a retainer wall 923 such that the retainer wall 923 and lever 191 define a gap 192. The lever 191 includes an upper surface 193a and lower surface 193b that faces the retainer wall 923. The upper surface 193a defines the chamber 919 and engagement recesses 196 (one numbered) that receive and couple the legs 779a and 779b of the locking member 972 to the lever 191. The lever 191 includes an actuation tab 194 that extends outward from the retainer 986 and through a slot (not shown) in the bearing member 84. When the actuation tab 194 is depressed in the lateral direction A toward the retainer wall 923, the locking member 974 is decoupled from the strap 32 so that the teeth 48 disengage from the teeth 978 of the locking member 974. When the locking member 974 is decoupled from the implant 24, the instrument 922 can advance along the strap 32 in the distal and/or proximal directions 9 and 7 as needed. When the actuation tab 194 is released, the lever 191 is biased toward the strap 32 so that teeth 178 of the locking member 974 engage the teeth 48 of the strap 32.

Figure 17:
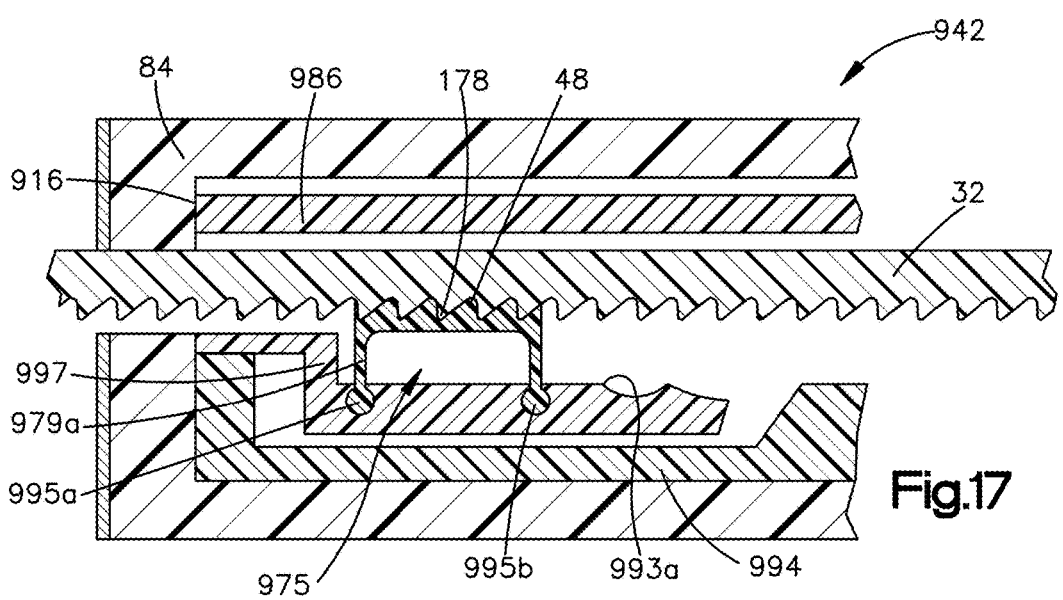
FIG. 17 is a partial plan sectional view of an instrument according to another embodiment of the present disclosure.

Turning to FIG. 17, an instrument 942 according to another embodiment of the disclosure is configured to permit the selective release of the attached portion of the implant 24 from the retainer 986. The instrument 942 is similar to the instrument 922 described above and the description of instrument 942 below will use the same reference numbers for elements that are common between instruments 922 and instrument 942, such as the actuator 82, bearing member 84, and the cutting assembly 120. In accordance with the alternative embodiment, the retainer 986 includes a lever 990 configured to move to the locking member 975 into and out of engagement with the strap 32. The retainer 986 includes a distal end 916 and a coupler 997 connects the distal end 916 to the lever 990. The lever 990 includes an upper surface 993 that defines and recesses 995a and 995b for receiving the legs 979a and 979b of the locking member 975.

Figure 18A:
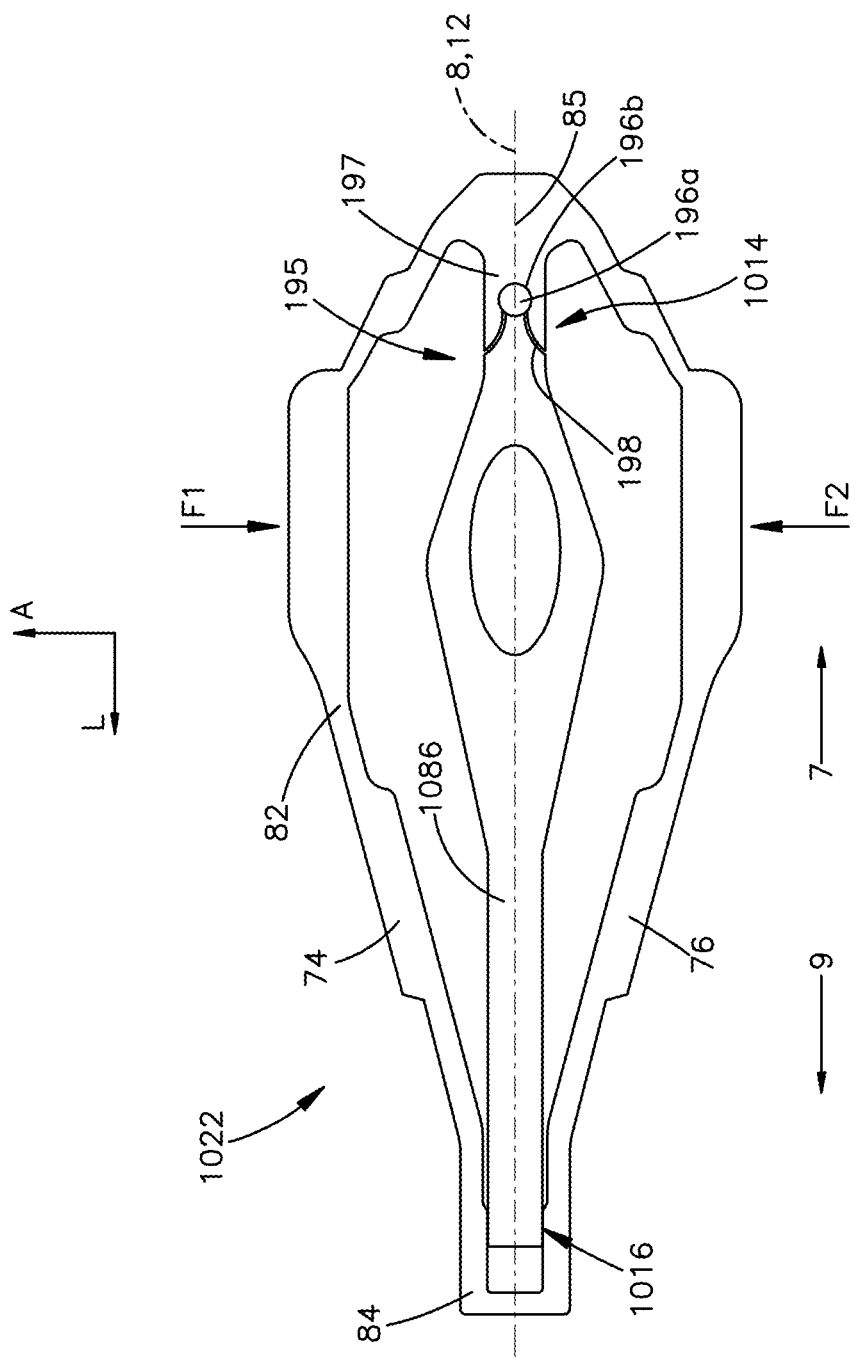
FIG. 18A is a plan view of an instrument according to another embodiment of the present disclosure.

Turning to FIG. 18A, another embodiment of an instrument 1022 is configured similar to the instrument 22 described above. The description below with respect to instrument 1022 will use reference numbers for elements that are common to instrument 22 and 1022. In accordance with the illustrated embodiment, the instrument 1022 includes a limiter assembly 195 that operates to limit displacement of the retainer 1086 in the proximal direction 7 when the actuator 82 is in the actuated configuration. For instance, when the retainer 1086 is attached the implant 24 and the actuator 82 is actuated so as to translate the retainer 1086 relative to the bearing member 84 in proximal direction 7, the force limiter assembly 195 prevents further increase of the distance X (not shown) between the bearing element 84 and the select location 85 of the actuator 82, which prevents further displacement of the retainer 86 and the retained portion of the implant 24. Accordingly, the limiter assembly 195 can prevent the implant 24 from being excessively tightened around the bone segments 28a and 28b. In osteoporotic bone, for example, there is risk that the strap 32 can pulled through the locking mechanism 38 to such an extent that the loop 55 cuts into the bone segments 28a and 28b. The force limiter assembly 195 is configured to prevent advancement of the strap 32 through the locking mechanism 38 beyond the point at which the bone fixation member 24 would cut into bone.

The force limiting assembly 195 illustrated in FIG. 18A can include a first release member 196a releaseably coupled to a second release member 196b. The first and second release members 196a and 196b are coupled during operation of the instrument 1022 as described above, yet are configured to decouple when the force applied along the retainer 1086 exceeds a predetermined threshold. For example, the threshold may be 420 N. The threshold can be adjusted as needed and thus can be higher or lower than 420 N. The proximal end 1014 of the retainer 1086 can define the first release member 196a and the proximal end 68 of the instrument 1022 can define the second release member 196b. Specifically, the instrument 1022 can include a projection 197 that extends toward a projection proximal end 198 in the longitudinal direction L away from the select location 85 of the actuator 82. The projection 197 can define the second release member 196b in the form a curved recess that extends into the projection 197 in the proximal direction 7. The first release member 196b can be configured as a curved node that has a shape complementary to the curved recess defined by the projection 197. The projection proximal end 198 may extend at least partially around the curved node when the retainer 86 is coupled to the instrument body 64. It should be appreciated that while the first release member 196b can define the curved node and the second release member 196b can define the curved recess, the first release member 196a can define the curved recess and the second release member 196b can define the curved node. For instance, either the retainer or instrument body can define the curved recess. Further, either the retainer or the actuator can define the curved node.

Continuing with FIG. 18A, in operation, the first and second release members 196a and 196b decouple when the tensile force applied along the retainer 86 exceeds the predetermined threshold as the retainer 1086 and retained portion of the implant 24 is being translated into the retracted position (not shown). As noted above, the instrument 922 applies a tensile force along the retainer 86 and the implant 24 in the distal direction 9 when 1) the retainer 86 is attached to the implant 24, and 2) forces F1, F2 are applied to actuator 82 along the lateral direction A so that the retainer 1086 translates relative to the bearing member 84 into the retracted position. As the force increases up to the predetermined threshold, the projection proximal end 198 biases outwardly and releases the curved node 196a from the curved recess 196b. When the curved node 196a is released, the retainer 1086 is no longer coupled to the proximal end 68 of the instrument body 64 and will no longer translate relative to bearing member 84. In this regard, the first and second release members 196a and 196b are configured as the force limiter assembly 195.

Turning to FIG. 18B, the instrument 1062 is configured similarly to instruments 22 and 1022 described above. In accordance with the alternative embodiment, the instrument 1062 can includes a force limiter assembly 1095 according to another embodiment. The force limiter assembly 1095 can be configured as a biasing member 1097 that can resist displacement of the actuator 82 in the proximal direction 7 when the actuator is in the second or actuated configuration.

For instance, when the retainer 2086 is attached the implant 24 and the actuator 82 is actuated so as to translate the retainer 2086 relative to the bearing member 84 along the longitudinal direction L, the force limiter assembly 1095 can prevent further displacement of retainer 2086. In accordance with the illustrated embodiment, the biasing member 1097 couples the proximal end 2014 of the retainer 2086 to the proximal end 68 of the instrument 1062. The biasing member 1097 can define a spring length S1 (not shown) that extends from the proximal end 2014 of the retainer 2086 to toward the select location 85. The biasing member 1097 can be a curved body configured to function as a tension spring. In other embodiments, the biasing member 1097 can be a coiled tension spring coupled between the proximal end 2014 of the retainer 86 and the actuator 82. The biasing member 1097 can be any other structure or device that deforms in response to an applied load. In operation, the force limiter assembly 1095 illustrated in FIG. 18B is configured to limit the force applied to retainer 2086 and thus the implant 24 via the biasing member 1097. As noted above, as the force is applied along the retainer 86 increases, the biasing member 1097 is extended from a first spring length S1 to a second spring length S2 (not shown) that is greater than the first spring length S1. The biasing member 497 can be configured with spring constant that limits further translation of the retainer 2086 when the tensile force meets a predetermined threshold, such that biasing member 1097 does not extend beyond a spring length S2. It should be appreciated that any type of biasing member can be used as a force limiter.

Turning now to FIGS. 19 through 25, other embodiments of the present disclosure includes bone fixation systems 200 and 300. Bone fixation system 200 and 300 includes respective bone fixation implants 210 and 310 each of which are configured secure a first bone segment 204, such as a bone flap, and to a second bone segment 206, such as a skull following a craniotomy. The bone fixation systems 200 and 300 include instruments 250 and 350, respectively, configured to apply a tensile force the implants 210 and 310 to secure the implants 210 and 310 against the bone segments.

Referring to FIGS. 19-22, the bone fixation system 200 can include the bone fixation implant 210 and a tensioning instrument 250 configured to urge the bone fixation implant into a clamping configuration against the bone segments 204 and 206. The bone fixation implant 210 can be configured as a cranial flap clamp that includes a first clamping member 212, a second clamping member 214, and a coupling element 216 that extends from the first clamping member 212 along a first direction 201 that is angularly offset with respect to outer bane facing surface of the first clamping member 212. The coupling element 216 is configured to be coupled to an actuator 252 of the tensioning instrument 250. The bone fixation implant 210 can be made of any material suitable for medical use, such as stainless steel, titanium, a titanium based alloy, or a resorbable polymeric material.

Figure 20:
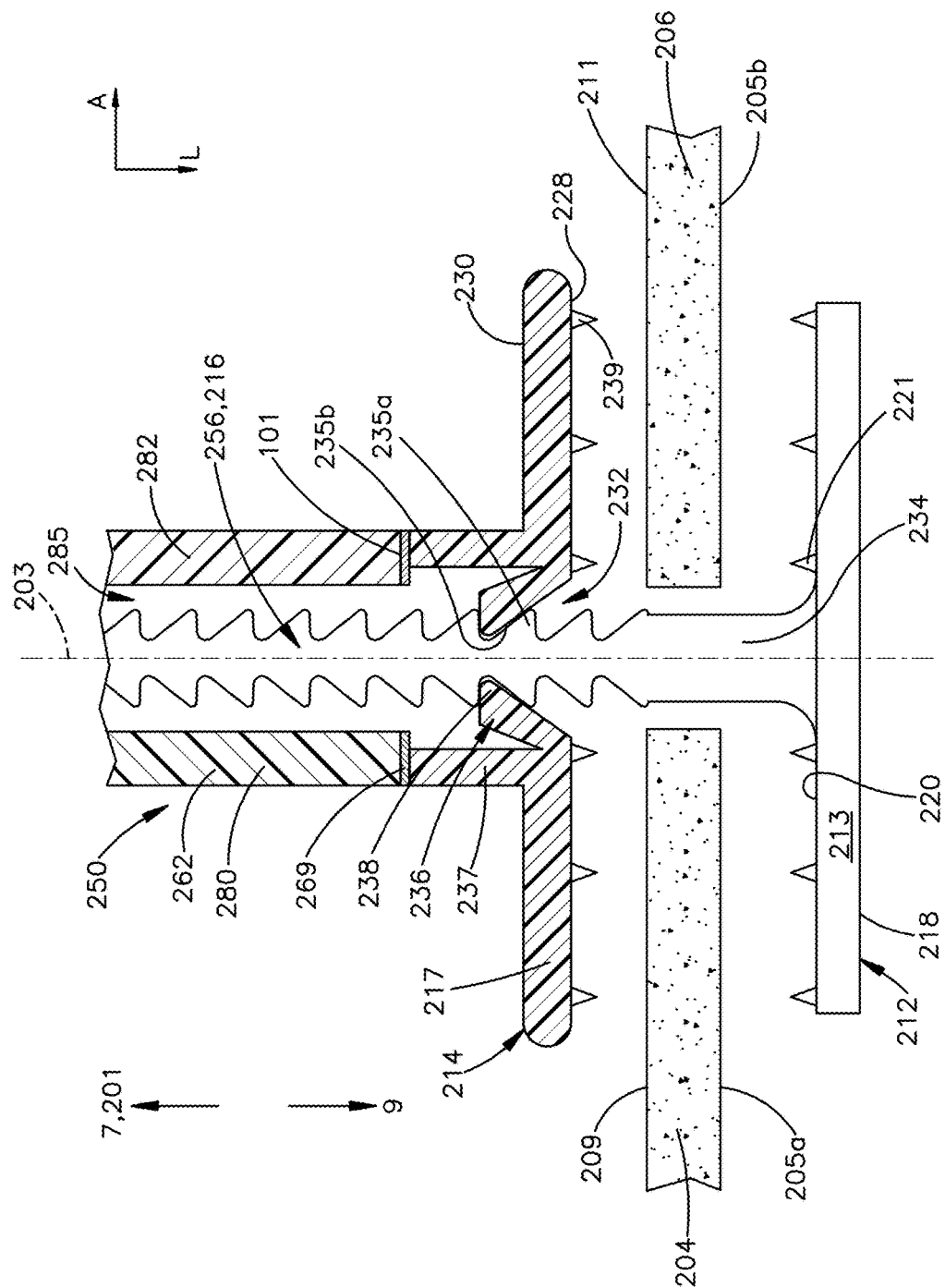
FIG. 20 is a detailed sectional plan view of the bone fixation system shown FIG. 19.

Referring to FIG. 20, the first clamping member 212 can include a first clamp body 213 having a first or inner surface 218 and a second or outer bone facing surface 220. The inner surface 218 may be convex and the outer surface 220 may be concave. The outer bone surface 220 may include one or more engagement teeth 221 configured to engage with inner surfaces 205a and 205b of the bone segments 204 and 206, respectively.

The second clamping member 214 includes a second clamp body 217 that defines an inner bone facing surface 228, an outer surface 230 opposed to the inner bone facing surface 228, and a bore 232 that extends along a bore axis 207. The body 217 includes a wall 237 that defines the bore 232. The second clamp body 217 can define a support surface 269. The wall 237 carries a locking member 236 that extends into the bore 232. The locking member 236 may be one or more engagement teeth 238 that project toward the bore axis 207. Further, the bone facing surface 228 of the second clamping member 214 can carry engagement teeth 239 that extend toward the outer bone surfaces 209 and 211 along a direction toward the first clamp member 212. The engagement teeth 239 can engage with the outer surfaces 209 and 211 the bone segments 204 and 206, respectively.

Figure 19:
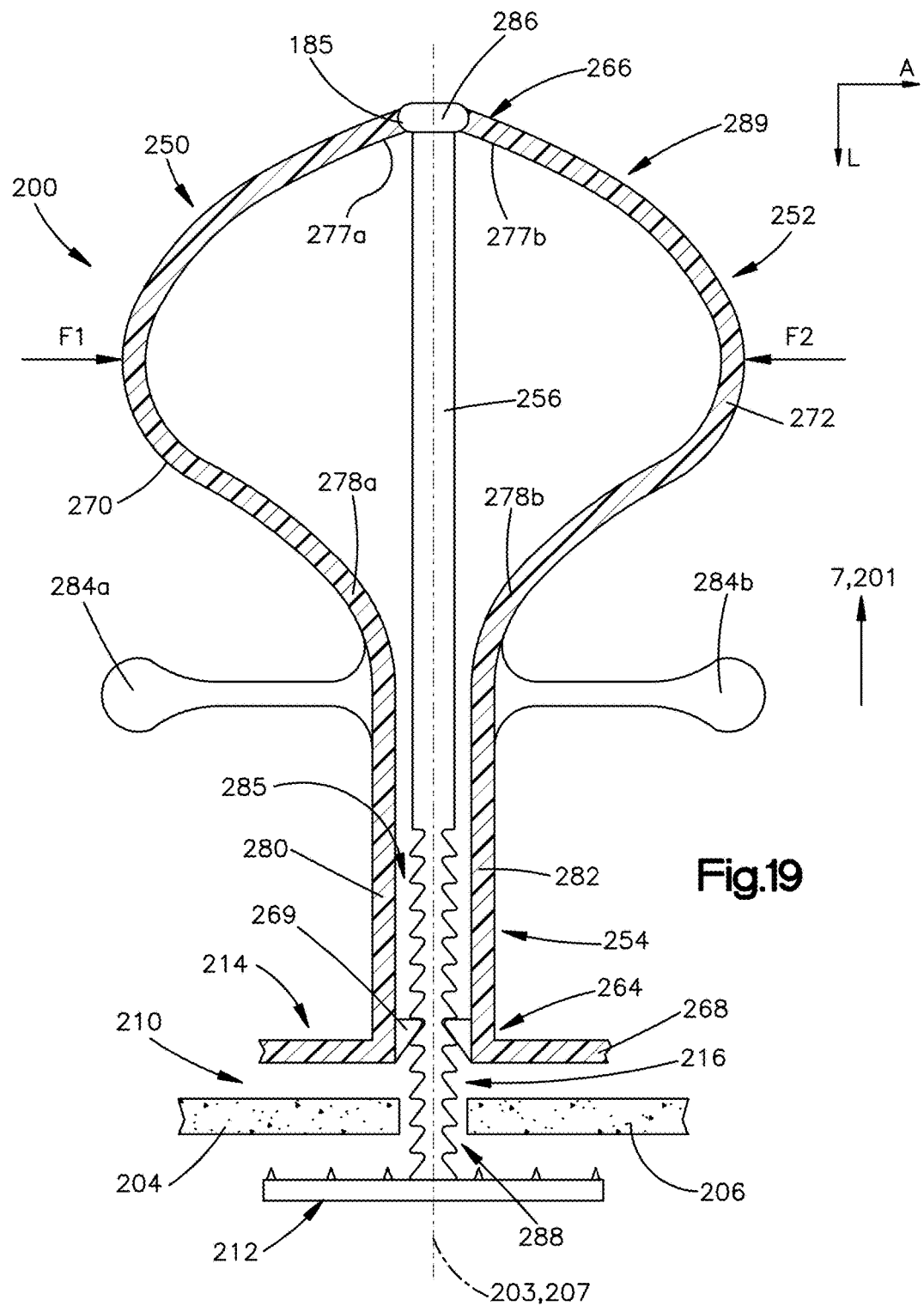
FIG. 19 is a plan view of a bone fixation system according to another embodiment of disclosure, showing a cross-section of a bone implant and a bone.

Referring now to FIGS. 19 and 20, the coupling element 216 extends from the first clamping member 212 along a proximal direction 7. In accordance with the illustrated embodiment, the coupling element 216 extends from the first clamping body 213, through the bore 232 of the second clamping body 217, and attaches to the actuator 252 at the selection location 185. The coupling element 216 can include an outer surface 234 that defines one or more engagement teeth 235a and notches 235b. When the coupling element 216 extends through the bore 232, the wall engagement teeth 238 engage the notches 235b defined by the coupling element 216. The teeth 235a and 238 are configured so that the coupling element 216 can translate through the bore 232 along an axis 203 in the proximal direction 7 while preventing the coupling element 216 from translating in the opposite distal direction 9. The coupling element 216 can be monolithic to the first clamping body 213 or it can be attached to the first clamping body 213 using any number of known methods.

Figure 21:
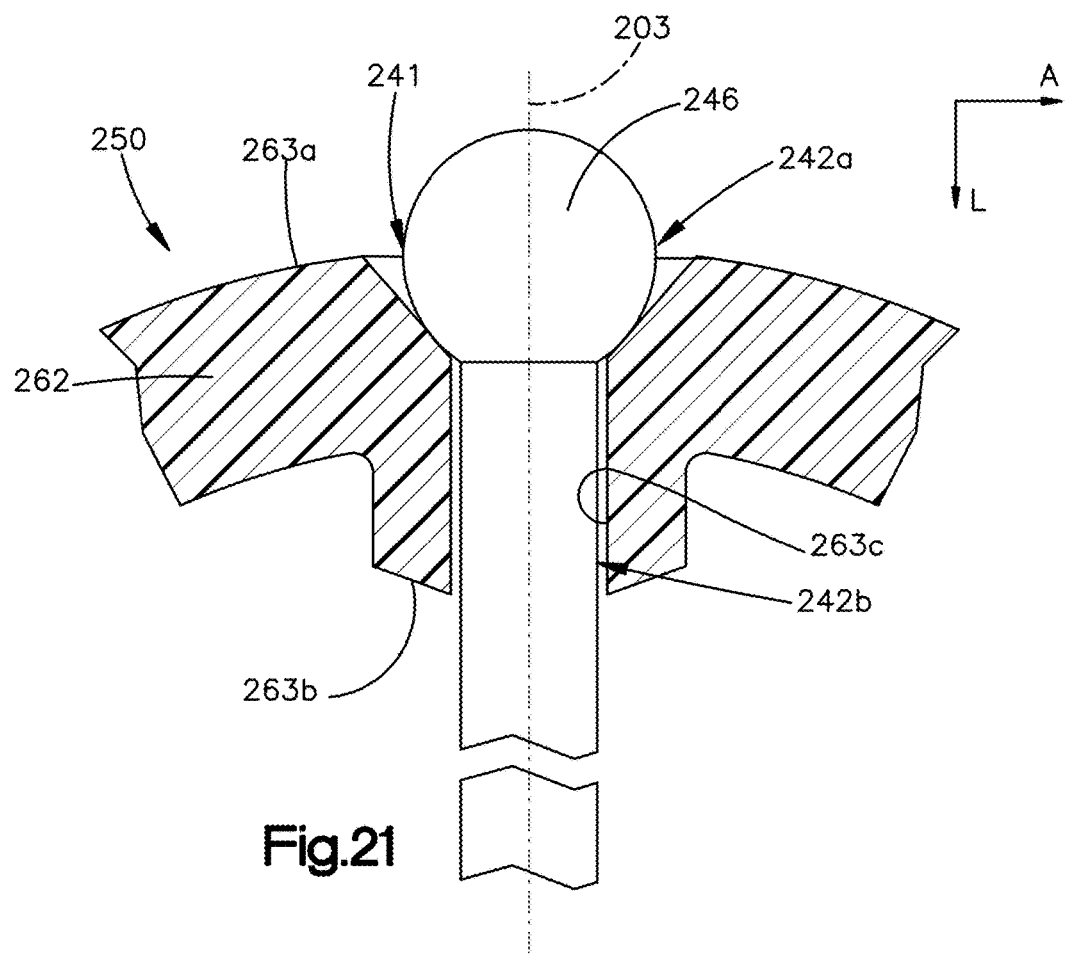
FIG. 21 is a detailed side view of a portion of the bone fixation system shown in FIG. 19.

The tensioning instrument 250 includes a bearing member 254 and an actuator 252 spaced from the bearing member 254 in the proximal direction 7 that is aligned with the longitudinal direction L. The tensioning instrument 250 includes an instrument body 262 that defines a distal end 264, and an opposed proximal end 266 spaced from the distal end 264 along the longitudinal direction L. The actuator 252 extends from the proximal end 266 to the bearing member 254. The instrument distal end 264 can define the bearing member 254. As discussed above, the actuator 252 can define the select location 185, which may be the location from where the coupling element 216 is attached to and extends from the actuator 252. The instrument 250 may include a cutting assembly that includes at least one blade 101 carried by the bearing member 254 and configured to cut the retained portion of the bone fixation implant 210 (or coupling element) when the bone fixation implant 210 has been urged into the clamping configuration (FIG. 21). Further, the instrument 250 may include a limiter assembly that is similar to the limiter assemblies 195 and 1095 described above and illustrated in FIGS. 18A and 18B.

The actuator 252 is configured to, in response to application of the compresses forces F1 and F2, transition from a first configuration, wherein a portion of the actuator 252 is spaced from the retainer in direction perpendicular to the proximal direction, into the second actuated configuration, wherein the portion of the actuator deforms so as to increase the distance between the selection location 185 and the bearing member 254. The actuator 252 includes flexible portion 289 that deforms when the forces F1 an F2 are applied thereto. The actuator flexible portion 289 includes a first actuation member or first arm 270 and a second actuation member or second arm 272 opposed to the first actuation member 270. In accordance with the illustrated embodiment, the first and second actuation members 270 and 272 may flex at spaced apart locations along each actuation member when the compressive forces F1, F2 are applied to the actuator 252. Accordingly, the first and second actuation members 270 and 272 may include one or more articulations 274 (not shown), such as a plurality of articulations. The first and second actuation members 270 and 272 include proximal ends 277a and 277b and opposed distal ends 278a and 278b, respectively. Actuation member proximal ends 277a and 277b may be disposed adjacent the proximal end 266 of the instrument body and actuation member distal ends 278a and 278b may be adjacent to the bearing member 254. In alternative embodiments, the first and second actuation members 270 and 272 can be curved so as to extend along a curved axis, similar the actuation members 74 and 76 described with respect to instrument 22. The actuator 252 can therefore have a similar structure to and function similar to the actuator 82.

Turning to FIG. 20, the bearing member 254 is configured to abut the support surface 269 of the second clamp body 217 so as to brace the instrument 250 for actuation and displacement of the attached coupling element 216. The bearing member 254 of the instrument 250 includes spaced apart walls 280 and 282. The walls 280 and 282 define a channel 285 that extends along the longitudinal direction L and is sized and configured to receive a portion of the bone fixation implant 210, for instance the coupling element 216. At least the walls 280 and 282 may carry one, for instance a pair of blades 100. The instrument body 262 also includes gripping members 284a and 284b (FIG. 19) that extend from the walls 280 and 282 along the lateral direction A.

Referring to FIGS. 19-22, the coupling element 216 may be elongate along an axis 203 and further defines a proximal end 286 and a distal end 288 spaced from the proximal end 286 along the axis 203. The coupling element proximal end 286 may be coupled to the location 185 of the actuator 252. The coupling element distal end 288 can be attached to or monolithic with first clamp body 213. In alternate embodiments, the instrument 250 can include a retainer that extends from the location 185 toward the bearing element. In such an embodiment, the coupling element proximal end 286 can be attached to the retainer.

Figure 22:
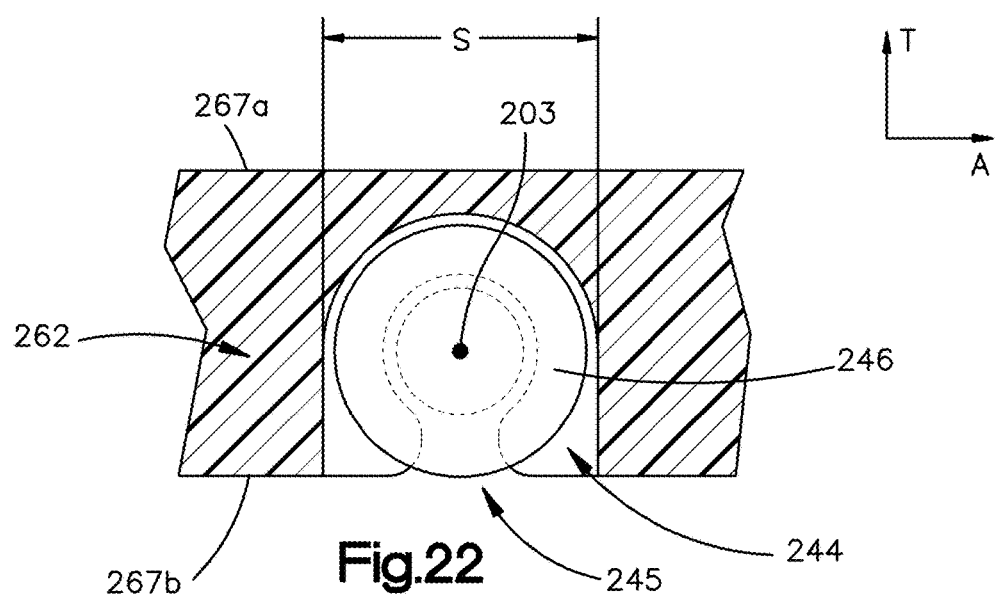
FIG. 22 is a detailed end view of the bone fixation system shown in FIG. 19.

Turning to FIGS. 21 and 22, the instrument body 262 can define a throughbore 241 sized to receive the coupling element proximal end 286. The instrument body 262 includes an outer body surface 263a, an inner body surface 263b, and a transverse surface 263c that extends between the outer and inner body surfaces 263a and 263b. The transverse surface defines the throughbore 241. The throughbore 241 includes a proximal portion 242a and a distal portion 242b spaced from the proximal portion 242a along the axis 203 toward the distal end 268. The instrument body 262 includes opposed sides surfaces 267a and 267b spaced apart along the transverse direction T. The cavity 244 extends from the surface 267b in the transverse direction T toward surface 267a, and from the surface 263b toward surface 263a in the instrument longitudinal direction L so to define the open cavity 244. For instance, the cavity 244 is open to define a U-shaped cavity (FIG. 20b). The throughbore 241 thus defines a neck 245 between the proximal portion 242a and distal portions 242b of the throughbore 241. The cavity 244 has a first cross-sectional dimension Z that extends from a first point along surface 263c to an opposing point on surface 263c along a lateral direction A. The proximal end 286 of the coupling element 216 carries an expanded bearing member 246 sized to fit within the cavity 244. When the expanded bearing member 246 is seated in the cavity 244, the coupling element 216 is coupled to the instrument body 262 such that compressing the actuator 252 causes the coupling element 216 to translate along the axis 203 in the proximal direction 7, thereby clamping the bone segments 204 and 206 between the first and second clamp members 212 and 214. Further, because the cavity 244 is open along the side surface 267b, the bearing member 246 can bias into and out of engagement with instrument body 262 as needed. For instance, the coupling element 216 can be inserted through the bore 232 of the second implant member 214 into the cavity 244.

In accordance with an embodiment, the instrument 250 is configured so that when opposing compressive forces F1 and F2 are applied to the flexible portion 289 of the actuator 252 along the lateral direction A, the coupling element 216 is displaced the relative to the bearing member 254 in the proximal direction 7, 201. Displacement of the coupling element 216 in the proximal direction 7 urges the first clamp member 212 and the second clamp member 214 toward each other.

Figure 23:
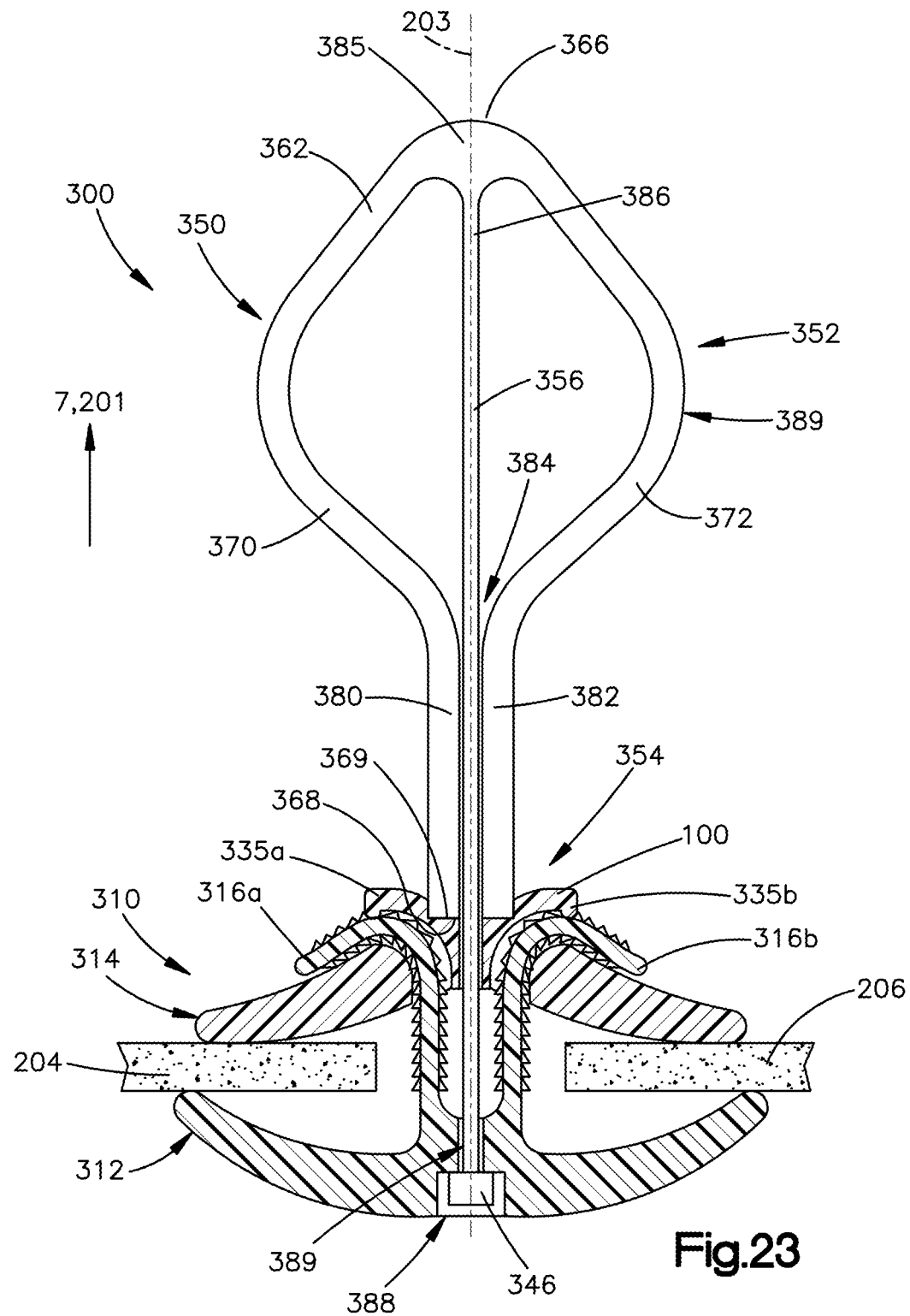
FIG. 23 is a side view of a bone fixation system, according to an embodiment of disclosure, showing a cross-section of a bone implant and a bone.

Turning now to FIGS. 23-25, the bone fixation system 300 include the bone fixation implant 310 and a tensioning instrument 350 configured to urge the bone fixation implant 310 into a clamping configuration against the bone segments 204 and 206. The bone fixation implant 310 includes a first or inner clamping member 312 and a second or outer clamping member 314. The bone fixation implant 310 can include a clamp engagement assembly 311 that extends from the inner clamping member 312 and is configured to engage the second clamping member 314. The bone fixation implant 310 can be made of any suitable biocompatible material as noted above.

Turning to FIGS. 23 and 24, in accordance with the illustrated embodiment, the first clamping member 312 includes a first clamp body 313 having an inner surface 318 and an outer bone facing surface 320. The inner surface 318 may be convex and the outer surface 320 may be concave. The outer surface 320 may include one or more engagement teeth (not shown) configured to engage with the inner surfaces 205a and 205b of the bone segments 204 and 206. The first clamp body 313 defines throughbore 338 that extends along the axis 203. The throughbore is sized to receive a distal end 388 of the instrument 350, such as a retainer 356. The throughbore 338 includes a proximal portion 339a and a distal portion 339b spaced from the proximal portion 339a along the axis 203. The distal portion 339a defines a cavity 340.

Continuing with FIGS. 23 and 24, the second clamping member 314 includes a second clamp body 317 that defines an inner bone facing surface 328 and an outer surface 330 opposed to the inner bone facing surface 328. The second clamp body 317 defines a central opening 332c that is aligned with the throughbore 338 of the first clamp body 313 along the axis 203, and the first and second openings 332a and 332b spaced from the central opening 332c. The central opening 332c can receive therethrough the retainer 356. The first and second openings 332a and 332b extend along curved bore axes (not shown) in a direction away from the axis 203. The second clamp body 317 includes a pair of guide members 335a and 335b coupled to or monolithic with the body 317 and are configured to span across the openings 332a and 332b (FIG. 25) and are spaced from the outer surface of the clamp member 314 so as define respective path that is aligned with the openings 332a and 332c. The first and second openings 332a and 332b are configured to receive and guide the engagement assembly 311.

In accordance with the illustrated embodiment, the engagement assembly 311 is monolithic with the first clamping member 312 or it can be attached to the first clamping member 312 and can extend through the second clamp member 314. The clamp engagement assembly 311 includes at least one flexible member, for instance first and second flexible members 316a and 316b. The first and second flexible members 316a and 316b are configured to extend through the first and second openings 332a and 332b of the second clamp member 314, respectively. Because the first and second flexible members 316a and 316b are configured similarly, only the flexible member 316a is described herein for ease of illustration. The flexible member 316a includes a body 319 that includes a base 322, a terminal end 324 spaced from the base 322 along the axis 321, and an outer surface (not numbered). The body 319 can carry one or more engagement members 326, such as teeth. The engagement members 326 are configured to couple to the second clamp member 314. For instance, the engagement members 326 can engage with an inner surface (not numbered) of the second clamp body 317 in the opening 332 or the guide members 335a. The engagement member 326 is configured to couple to the second clamp member 314 so as to 1) permit the flexible member 316a to translate through the opening 332a along the bore axis in a first direction, and 2) prevent the flexible member 316a from reversing direction and translating out the opening 332a in a second direction that is opposite the first direction.

The tensioning instrument 350 is configured to attach to a portion of the implant 310, and upon actuation of the instrument, urge the first and second clamp members 312 and 314 toward each other so as to clamp the bone segments 204 and 206 together. The instrument 350 is similar to the instrument 22 and instruments 250 describe above. For instance, the instrument 350 includes a bearing member 354 and an actuator 352 spaced from the bearing member 354 in in the longitudinal direction L, and a retainer 356 that extends from a location 385 of the actuator 352 toward the bearing member 354 and is configured to attach to a portion of the bone implant 310. Unlike instrument 250 described above where the coupling element 216 can be part of the implant 210, the retainer 356 can be part of the instrument 350 and can be attached to the implant 310. Further, the instrument 350 may include a cutting assembly, such as blade 101 that is configured to cut the portion of retainer 356 after the bone fixation implant 310 has been urged into the clamping configuration. The instrument can also include a force limiter assembly that is similar to the force limiter 195 and 1095 described above and illustrated in FIGS. 18A and 18B.

The instrument 350 includes an instrument body 362 that includes a proximal end 366 spaced from the bearing member 354 along the longitudinal direction L, such that body 362 defines at least a portion of the actuator 352 and at least portion of the bearing member 354. The bearing member 354 includes a distal surface 368 of that is configured to abut the support surface 369 of the second clamp member 314 and brace the instrument 350 against the second clamp member when the actuator 352 is actuated as discussed below.

The actuator 352 can include a flexible portion 389 that can be deformed so as to cause the location 385 to move in the proximal direction 7 away from the bearing member 354. The location 185 and bearing member 354 can define a distance extending therebetween as described above in connection with instrument 22 and FIGS. 4A-4D. As such, deformation of the actuator 352, and in particular of the flexible portion 389, causes the distance between the location 185 and the bearing member 354 to increase.

The flexible portion 389 can include first and second actuation members 370 and 372. The first and second actuation members 370 and 372 can be curved so to extend along curved axes with respect to a point (not shown) defined by the retainer 356. The actuator 352 can therefore transition from the first configuration where the first and actuation members 370 and 372 are spaced apart from the retainer 356 and have a first or a curved shape, into an actuated configuration where the actuation members 370 and 372 are deformed and have a second or more linear shape and positioned toward the retainer 356. In an alternative embodiment, the first and second actuation members 370 and 372 may include at least one articulation (not shown), such as a plurality of articulations. Thus, the first and second actuation member 370 and 372 can be constructed and function similar to the first and second actuation members 72 and 74 described above with respect to instrument 22.

In accordance with the illustrated embodiment, the retainer 356 extends from the proximal end 366 of the instrument body 362 toward the bearing member 354 through the opening 332c and is coupled the first clamp member 312. The retainer 356 is elongate along the axis 203 and further defines a retainer proximal end 386 and a retainer distal end 388 spaced from the retainer proximal end 386 along the axis 203. The retainer distal end 388 is attached to the first clamping member. The distal end 388 of the retainer 356 includes an enlarged portion 346 sized to fit within the cavity 340 of the first clamping member 312.

Continuing with FIGS. 23 and 24, in operation, the bearing member 368 can abut the surface 369 of the second implant member 314 when the actuator 352 is in the first configuration. Compressing the actuator 352 in a direction toward the retainer 356 deforms the flexible portion 389 and causes the location 185 to displace away from the bearing member 354. Displacement of the location 185 of the actuator 352 causes the retainer 356 to translate through the opening 332c relative to the bearing member 354 in the proximal direction 7. The distal end 388 of the retainer 356 then urges the first clamping member 312 to advance toward the bone surface 205, while the second clamping member 314 advances toward the opposing bone surfaces 209 and 211. As the retainer 356 translates through the second clamp member 314, the flexible members 316a and 316 translate through the respective openings 332a and 332b and slide along the surface 330 away from the axis 203 so that the terminal ends 322a and 332b are oriented toward an outer periphery of the clamping member 314 positioning the bone fixation implant 310 in the clamping configuration. Thereafter, the instrument 350 can be rotated about axis 203 to cause the blade 101 to cut the retainer 356, leaving the implanted bone fixation implant 310 as shown in FIG. 25. An alternative to cutting the retainer 356 is to bias the bearing member 346 out of engagement with the cavity 340 and pull the retainer through the opening 332c. In such an embodiment, the engagement assembly 311 is configured to lock the first clamp member 312 to the second clamp member 314.

With respect to the bone implants 210 and 310 described above and shown in FIGS. 19-25, reference to "first" or "second" are used for purposes of illustrating the various embodiments of the bone fixation system 210, 310. Thus, the inner clamp member 212, 312 can be referred to as a first clamp member or a first portion of the implant 210, 310 and the outer clamp member 214,314 can be referred to as the second clamp member or a second portion of the implant 210,310. Alternatively, the inner clamp member 212, 312 can be referred to as a second clamp member or a second portion of the implant 210, 310 and the outer clamp member 214,314 can be referred to as the first clamp member or a first portion of the implant 210,310.

Another embodiment of the present disclosure can include a method for applying tension to an element. The element can be an implant or a portion of the implant, such as the implant 24 shown in FIGS. 1-18B, such that the method can be performed using any one of the instruments illustrated in FIGS. 1 through 18B. In addition, the element can be the implant shown with bone fixation system 300 illustrated in FIGS. 23-25, such that the method can be performed using instrument 350 illustrated in FIGS. 23-25. The method includes placing a bearing member, such as bearing member 84 or any other similar bearing member, against a first portion of the element. A second portion of the element can be coupled to the retainer, for instance retainer 86, or any other similar retainer described above. When the second portion of the element is coupled to the retainer, the retainer extends from a location of the actuator that is spaced from the bearing member in a proximal direction. The actuator can be similar to the actuator 82 or other similar actuators described above. The method can include the step of applying an actuation force to the portion of the actuator toward the retainer, causing the actuator to deform and move the location of the actuator and the retainer relative to the bearing member in the proximal direction, thereby applying a tensile force to the second portion of the element. The applying step can further include moving the retainer from a first position relative to the bearing member to a second position that is spaced from the first position in the proximal direction, thereby applying the tensile force to the second portion of the element. The method can include the step of limiting further movement of the retainer relative to the bearing member. In accordance with a particular embodiment of the method, the element is a bone fixation member, wherein the first portion of the element is a lock and the second portion of the element is a strap. In accordance with the embodiment of the method for applying tension to an element using the bone fixation system illustrated in FIGS. 23-25, the element is an implant, and the first portion is a first bone implant configured to face a first surface of a bone, the second portion is a second bone implant that is configured to face a second surface of the bone that is opposite the first surface. Such a method can include and the coupling the retainer to the second bone implant.

Another embodiment of the present disclosure includes a method for securing an implant to bone using the bone fixation system illustrated in FIGS. 19-22, which includes an implant having a first portion configured to face a first surface of a bone, a second portion configured to face second surface of the bone that opposite the first surface, and a coupling element that extends from the second portion through the first portion of the implant. In accordance with such an embodiment, the method includes placing a bearing member against the first portion of the implant. The method includes attaching the coupling element to the actuator at a location that is spaced from the bearing member in a proximal direction, such that a flexible portion of actuator is spaced from the coupling element in a direction that is perpendicular to the proximal direction. The method includes applying an actuation force to the flexible portion of the actuator toward coupling element, which causes the actuator move the coupling element relative to the bearing member in the proximal direction, thereby urging the second portion of the implant toward the first portion of the implant.

What is claimed:

1. An instrument comprising:
a bearing member configured to abut a first portion of an implant;
an actuator spaced from the bearing member in a proximal direction, the actuator including a flexible portion, the flexible portion including a first actuation member and a second actuation member that is opposed to the first actuation member in a direction that is perpendicular to the proximal direction; and
a retainer configured to attach to a second portion of an implant, the retainer extending from a location on the actuator toward the bearing member, the location spaced from the bearing member a distance in the proximal direction, wherein the retainer is configured such that a portion of the retainer is extendable within a receptacle defined by the bearing member, and the retainer is disposed between the first actuation member and the second actuation member,
wherein application of a force to the actuator deforms the flexible portion so as to increase the distance between the location and the bearing member.

2. The instrument according to claim 1, wherein the actuator includes a proximal end spaced from the bearing member in the proximal direction, the proximal end including the location, wherein the flexible portion is coupled to the proximal end of the actuator and to the bearing member, such that, when the flexible portion is deformed, the proximal end of the actuator is displaced relative to the bearing member, thereby increasing the distance between the location and the bearing member.

3. The instrument according to claim 1, wherein the retainer includes at least one locking member, the at least one locking member configured to attach the second portion of the implant to the retainer.

4. The instrument according to claim 3, wherein the at least one locking member carries a set of teeth configured to engage the second portion of the implant.

5. The instrument according to claim 1, wherein the bearing member carries at least one blade configured to cut the second portion of the implant when the second portion of the implant is attached to the retainer.

6. The instrument according to claim 5, further comprising a cutting assembly supported by the bearing member, the cutting assembly including the at least one blade and a blade actuator, wherein actuation of the blade actuator causes the at least one blade to cut the implant when the retainer is attached to the implant.

7. The instrument according claim 1, further comprising a force limiter configured to prevent the actuator from increasing the distance between the location of the actuator and the bearing member when a force along the retainer exceeds a predetermined force threshold when the retainer is attached to the second portion of the implant.

8. The instrument according to claim 7, wherein the force limiter is at least one of a release member and a biasing member.

9. The instrument according to claim 1, wherein the instrument is configured such that the flexible portion of the actuator deforms so as to increase the distance between the location and the bearing member responsive to the force applied to the actuator, wherein the force is directed toward the retainer.

10. The instrument according to claim 9, wherein the actuator is configured such that deformation of the flexible portion causes the distance to increase along a longitudinal direction that defines the proximal direction.

11. The instrument according to claim 1, wherein the instrument is configured such that the actuator transitions from a first configuration where the retainer is in a first position relative to the bearing member to a second actuated configuration where the retainer is in a second position relative to bearing member that is spaced from the first position along a longitudinal direction responsive to the force applied to the actuator, wherein the proximal direction is oriented along the longitudinal direction.

12. The instrument according to claim 11, wherein the first and second actuation members are elongate along respective first and second axes, wherein when the actuator is in the first configuration, the first and second actuation members are each curved such that each of the first and second axes define a respective curvature, and when the actuator is in the second actuated configuration, the first and second actuation members are deformed such that the respective curvature of the first and second axes decreases.

13. The instrument according to claim 11, wherein release of the force applied to the actuator permits the actuator to return to the first configuration such that the retainer returns toward the first position.

14. The instrument according to claim 11, wherein the first and second actuation members each include at least one articulation, and the first and second actuation members are bendable at each of the at least one articulation so as to cause the actuator to transition from the first configuration into the second actuated configuration.

15. The instrument according to claim 14, wherein the first and second actuation members each include at least one rigid member adjacent to a respective one of the at least one articulation, wherein the at least one rigid member is less flexible than the at least one articulation.

16. The instrument according to claim 11, wherein the portion of the retainer is received within the receptacle when the retainer is in the first position.

17. The instrument according to claim 1, further comprising a release actuator that is configured to selectively release the implant from the retainer when the retainer is attached to the second portion of the implant.

18. The instrument according to claim 1, wherein the implant includes a third portion, wherein the instrument further comprises a removable stabilization member configured to couple the third portion of the implant to the bearing member such that the second portion of the implant is attachable to the retainer.

19. The instrument according to claim 1, wherein the retainer is monolithic with the actuator.

20. The instrument according to claim 1, wherein the implant is a cable tie that includes a lock and a strap that extends from the lock, and the retainer is configured to attach to the strap.

* * * * *